US006462257B1

(12) United States Patent
Perera et al.

(10) Patent No.: US 6,462,257 B1
(45) Date of Patent: Oct. 8, 2002

(54) VICILIN-LIKE SEED STORAGE PROTEIN GENE PROMOTER AND METHODS OF USING THE SAME

(75) Inventors: Ranjan Perera, San Diego, CA (US); John Cairney, Decatur; Gerald S. Pullman, Alpharetta, both of GA (US)

(73) Assignee: Institute of Paper Science and Technology, Inc., Atlanta, GA (US)

( * ) Notice: Subject to any disclaimer, the term of this patent is extended or adjusted under 35 U.S.C. 154(b) by 0 days.

(21) Appl. No.: 09/323,195

(22) Filed: Jun. 1, 1999

(51) Int. Cl.[7] .......................... C12N 5/04; C12N 15/09; C12N 15/29; C12N 15/82; A01H 5/00
(52) U.S. Cl. ....................... 800/287; 800/278; 800/292; 800/293; 800/294; 800/295; 435/69.1; 435/468; 536/23.1; 536/23.6; 536/24.1
(58) Field of Search .................................. 800/278, 287, 800/292, 293, 294, 295; 435/69.1, 468; 536/23.1, 24.1, 23.6

(56) References Cited

U.S. PATENT DOCUMENTS

| 5,470,359 | A | | 11/1995 | Huffman ........................ 47/58 |
| 5,484,718 | A | | 1/1996 | Schofield et al. ......... 435/172.3 |
| 5,498,831 | A | * | 3/1996 | Burgess et al. ............. 800/205 |
| 5,514,584 | A | | 5/1996 | Lastick et al. ............ 435/252.3 |
| 5,525,716 | A | | 6/1996 | Olsen et al. ............... 536/24.1 |
| 5,543,576 | A | | 8/1996 | van Ooijen et al. ........ 800/250 |
| 5,589,614 | A | | 12/1996 | Bridges et al. ............. 800/205 |
| 5,593,963 | A | | 1/1997 | Van Ooijen et al. .......... 514/12 |
| 5,612,472 | A | | 3/1997 | Wilson et al. .............. 536/24.1 |
| 5,616,474 | A | | 4/1997 | Bolotin et al. ............. 435/69.1 |
| 5,633,439 | A | | 5/1997 | Walter ........................ 800/205 |
| 5,646,333 | A | | 7/1997 | Dobres et al. .............. 800/205 |
| 5,659,026 | A | | 8/1997 | Baszczynski et al. ...... 536/24.1 |
| 5,670,349 | A | | 9/1997 | Cramer et al. ........... 435/172.3 |
| 5,677,151 | A | | 10/1997 | Wilson et al. ................ 435/72 |
| 5,684,239 | A | | 11/1997 | Wu et al. .................... 800/205 |
| 5,689,053 | A | | 11/1997 | Robert et al. ............... 800/205 |
| 5,712,112 | A | | 1/1998 | Yu et al. ..................... 435/69.1 |
| 5,723,764 | A | | 3/1998 | Nichols et al. ............. 800/205 |

FOREIGN PATENT DOCUMENTS

| CA | 2014264 | 10/1990 |
| CA | 2192106 | 6/1997 |

OTHER PUBLICATIONS

Kim et al. Plant Molecular Biology, vol. 24, pp. 105–117, 1997.*
Ammirato, "The regulation of somatic embryo development in plant cell cultures: Suspension culture techniques and hormone requirements," Bio/Technology, 1983, 1, 68–74.
Ausubel et al., Current Protocols in Molecular Biology, John Wiley & Sons, New York, 1989, 2.3.1–2.3.3.
Bapat et al., "Occurrence and frequency of precocious germination of somatic embryos is a genotype–dependent phenomenon in wheat," Plant Cell Rep., 1988, 7, 538–541.
Becwar et al., "Initiation of embryogenic cultures and somatic embryo development in loblolly pine (Pinus taeda)," Can. J. For. Res., 1990, 20, 810–817.
Braun et al., "A vicilin–like seed protein of cycads: similarity to sucrose–binding proteins," Plant Mol. Biol., 1996, 31, 35–44.
Church et al., "Genomic sequencing," Proc. Natl. Acad. Sci. USA, 1984, 81, 1991–1995.
Crouch, "Non–zygotic embryos of Brassica napus L. contain embryo–specific storage protein," Planta, 1982, 156, 520–524.
da Silva et al., "A cotyledon regulatory region is responsible for the different spatial expression patterns of Arabidopsis 2S albumin genes," Plant J., 1994, 5(4), 493–505.
de Pater et al., "A 22–bp Fragment of the Pea Lectin Promotor Containing Essential TGAC–like Motifs Confers Seed–Specific Gene Expression," Plant Cell, 1993, 5, 877–886.
Gander et al., "Isolation, characterization and expression of a gene coding for a 2S albumin from Bertholletia excelsa (Brazil nut)," Plant Mol. Biol., 1991, 16, 437–448.
Goldberg et al., "Regulation of Gene Expression during Plant Embryogenesis," Cell, 1989, 56, 149–160.
Guerche et al., "Differential Expression of the Arabidopsis 2S Albumin Genes and the Effect of Increasing Gene Family Size," Plant Cell, 1990, 2, 469–478.
Higgins, "Synthesis and Regulation of Major Proteins in Seeds," Ann. Rev. Plant Physiol., 1984, 35, 191–121.
Kawagoe et al., "Synergism between CACGTG (G–box) and CACCTG cis–elements is required for activation of bean seed storage protein 3–phaseolin gene," Plant J., 1994, 5, 885–890.
Krochko et al., "Contrasting Storage Protein Synthesis and Messenger RNA Accumulation during Development of Zygotic and Somatic Embryos of Alfalfa (Medicago sativa L.)," Plant Physiology, 1992, 99, 46–53.
Laden et al., "Development regulation of beta–conglycinin in soybean axes and cotyledons," Plant Physiol., 1987, 84, 35–41.
Lessard et al., "Upstream regulatory sequences from two beta–conglycinin gene," Plant Mol. Biol., 1993, 22, 873–885.

(List continued on next page.)

Primary Examiner—Phuong T. Bui
Assistant Examiner—Medina A. Ibrahim
(74) Attorney, Agent, or Firm—Woodcock Washburn LLP

(57) ABSTRACT

The present invention provides novel vicilin-like gene promoters. The promoter of the present invention may be operably linked to a desired sequence such as a gene or fragment thereof. A promoter-gene construct is also embodied by the present invention. Methods of producing and expressing polypeptides in plants are also provided. The present invention further provides methods for monitoring the embryo development of conifers.

23 Claims, 11 Drawing Sheets

OTHER PUBLICATIONS

Muntz, "Developmental control of storage protein formation and its modilation by some internal and external factors during embryogenesis in plant seeds," *Biochem., Physiol. Pflnazen*, 1987, 182, 93–116.

Newton et al., "Vicilin–like seed storage proteins in the gymnosperm interior spruce (*Picea glauca/engelmanii*)," *Plant Mol. Biol.*, 1992, 20, 315–322.

Pang et al., "Molecular cloning, genomic organization, expression and evolution of 12S seed storage protein genes of *Arabidopsis thaliana*," *Plant Mol. Biol.*, 1988, 11, 805–820.

Pullman et al., "An Embryo Staging System for Comparison of Zygotic and Somatic Embryo Development," TAPPI R&D Division Biological Sciences Symposium, Minneapolis, Minnesota, Oct. 3–6, 1994, 31–33.

Senaratna et al., "Desiccation tolerance of alfalfa (*Medicago sativa* L.) Somatic embryos: Influence of abscisic acid, stress pre treatments and drying rates," *Plant Sci.*, 1989, 65, 253–259.

Shoemaker et al., "Storage protein accumulation patterns in somatic embryos of cotton (*Gossypium hirsutum* L.)," *Plant Cell Rep.*, 1987, 6, 12–15.

Shotwell et al., "The Biochemistry and Molecular Biology of Seed Storage Proteins," in *The Biochemistry of Plants: A Comprehensive Treatise*, Academic Press, San Diego, CA, vol. 15, Ch. 7, 1989, 297–345.

Steward et al., "Growth and development of cultured plant cells," *Science*, 1964, 143, 20–27.

Thomas, "Gene Expression During Plant Embryogenesis and Germination: An Overview," *Plant Cell*, 1993, 5, 1401–1410.

Thomas et al., "Identification of an Enhancer Element for the Endosperm–Specific Expression of High Molecular Weight Glutenin," *Plant Cell*, 1990, 2, 1171–1180.

Wallace et al., "Nucleotide Sequence of a cNDA Clone Corresponding to the Maize Globulin–2 Gene," *Plant Physiol.*, 1991, 95, 973–975.

Walling et al., "Transcriptional and post–transcriptional regulation of soybean seed protein mRNA levels," *Proc. Natl. Acad. Sci. USA*, 1986, 83, 2123–2127.

Wenck et al., "High–efficiency Agrobacterium–mediated transformation of Norway spruce (*Picea abies*) and loblolly pine (*Pinus taeda*)," *Plant Mol. Biol.*, 1999, 39(3), 407–416.

Miki et al., "Procedures for Introducing Foreign DNA into Plants," in *Methods in Plant Molecular Biology and Biotechnology*, Glick, B.R. et al. (eds.), CRC Press, Inc., 1993.

Sambrook et al., *Molecular Cloning, A Laboratory Manual*, Cold Spring Harbor Laboratory Press, NY, 1989.

\* cited by examiner

FIG. 1

```
             *        20         *        40         *        60
    ACTATAGGGCACGCGTGGTCGAcGGCCCGGGcTGGTAAA GTGTGTGTTTGCAGGGTGCAGA
53: ACTATAGGGCACGCGTGGTCGACGGCCCGGGCTGGTAAA-GTGTGTGTTTGCAGGGTGCAGA :61
54: ACTATAGGGCACGCGTGGTCGACGGCCCGGG-TGGTAAA-GTGTGTGTTTGCAGGGTGCAGA :60
51: ACTATAGGGCACGCGTGGTCGACGGCCCGGGCTGGTAAAAGTGTGTGTTTGCAGGGTGCAGA :62
52: ACTATAGGGCACGCGTGGTCGA-GGCCCGGGCTGGTAAAAGTGTGTGTTTGCAGGGTGCAGA :61

*        80         *       100         *       120
    TAATGGCAGCATGTATGACATTAGACATATGGCATTGGCAAATGCT TCGATTTTGGCACTC
53: TAATGGCAGCATGTATGACATTAGACATATGGCATTGGCAAATGCTATCGATTTTGGCACTC :123
54: TAATGGCAGCATGTATGACATTAGACATATGGCATTGGCAAATGCTATCGATTTTGGCACTC :122
51: TAATGGCAGCATGTATGACATTAGACATATGGCATTGGCAAATGCTGTCGATTTTGGCACTC :124
52: TAATGGCAGCATGTATGACATTAGACATATGGCATTGGCAAATGCTGTCGATTTTGGCACTC :123

*       140         *       160         *       180
    ATCACTGTAATTGTTGCAACATGTCAATCGTCtGCAaCATGCCCTGG GATCATAGGTTATG
53: ATCACTGTAATTGTTGCAACATGTCAATCGTCTGCAGCATGCCCTGGCGATCATAGGTTATG :185
54: ATCACTGTAATTGTTGCAACATGTCAATCGTCTGCAACATGCCCTGGCGATCATAGGTTATG :184
51: ATCACTGTAATTGTTGCAACATGTCAATCGTCTGCAACATGCCCTGGTGATCATAGGTTATG :186
52: ATCACTGTAATTGTTGCAACATGTCAATCGTCCGCAACATGCCCTGGTGATCATAGGTTATG :185

*       200         *       220         *       240
    CAAGAACTCAGA GtGTTCACCaTTCTTCAATACCAaATGCCTCTTCTGTCTGGTTGCTTCC
53: CAAGAACTCAGATGTGTTCACCATTCTTCAATACCAAATGCCTCTTCTGTCTGGTTGCTTCC :247
54: CAAGAACTCAGATGAGTTCACCATTCTTCAATACCAAATGCCTCTTCTGTCTGGTTGCTTCC :246
51: CAAGAACTCAGACGTGTTCACCATTCTTCAATACCATATGCCTCTTCTGTCTGGTTGCTTCC :248
52: CAAGAACTCAGACGTGTTCACCGTTCTTCAATACCAAATGCCTCTTCTGTCTGGTTGCTTCC :247

*       260         *       280         *       300
    ACCACGCGTCCATGCATG CATGATTCTCTTGTATATAAAAGTCCCCCTTGCCCATTCTGT
53: ACCACGCGTCCATGCATGCACATGATTCTCTTGTATATAAAAGTCCCCCTTGCCCATTCTGT :309
54: ACCACGCGTCCATGCATGCACATGATTCTCTTGTATATAAAAGTCCCCCTTGCCCATTCTGT :308
51: ACCACGCGTCCATGCATGTGCATGATTCTCTTGTATATAAAAGTCCCCCTTGCCCATTCTGT :310
52: ACCACGCGTCCATGCATGTGCATGATTCTCTTGTATATAAAAGTCCCCCTTGCCCATTCTGT :309

320         *       340
    CTAGTACC GACTTCACCAAAGCACCATCATG
53: CTAGTACC-GACTTCACCAAAGCACCATCATG :340
54: CTAGTACCAGACTTCACCAAAGCACCATCATG :340
51: CTAGTACCGGACTTCACCAAAGCACCATCATG :342
52: CTAGTACCGGACTTCACCAAAGCACCATCATG :341
```

FIG. 2

AAAGCACCATCATGGCTTTTGTTTCTTTACTTACCATTCTTCAAGCAATCTCCTCCTGCTCCGTT
GCTCTCACTGAGCCACTAGCCACTGTGGCCAATCAAGGAGTTTTTCCTGAAGATCATGGGCGA
GGGCACCAGAGACGAGAAGAAGAACGAGAGGAGAATCCGTACGTATTCCACAGTGACAGAT
TCAGGATGAGAGCGTCATCTGACGCTGGTGAAATCAGAGCTCTCCCCAACTTTGGTGAGGCCT
CTGAACTTCTTGAAGGGATTAGTAAATACAGAGTTACCTGCATTGAAATGAGACCCAACACGG
TCATGCTCCCTCACTATCTTGACGCGACATGGATTTTATATGTTACTGGAGGAAGAGGTTACAT
AGCTTACGTGCACCAGAATGAACTGGTGAAAAGAAAGTTGGAGGAAGGAGATGTATTTGGTG
TTCCAAGTGGTCATACATTTTATCTCGTTAACAACGATGACCACAACAGCCTTCGCATTACCA
GTCTCCTGCGTACAGTGTCTACGATGCGAGGAGAATATGAGCCCTACTACGTTGCTGGAGGTC
GGAATCCTGAGACTGTTTACTCTGCCTTTAGCGATGATGTTCTCGAAGCTGCATTCAATACGA
ACGTTATAGAAGCTAGAACACATTTTCCGGTGCACATAGAACGGGAGTCATATTCCATGGCAA
ATGAAGAACAGATTAGAGAAATGTTGAGGAAACGGGGATTTTCAGCAGAATCCATGTCTGCA
TCTGAGCACCCAAAGCCTTTTAACCTTCGGAACCAGAAGCCAGATTTCGAGAACGACAATGGC
AGGTTTACTAGAGCTGGTCCCAATGAAAATCCTCTTCTTGACGCGGTCGATGTTACTGCTGGG
TTTGGCGTTTTGAATCCTGGAACCATGACAGCCCCATCTCACAACACGAAAGCAACCTCAATC
GCCATTGTCACACAGGGGGAGGGAAGGATTGAGATGGCGTGCCCGCACCTTGGTCAACATGG
CTGGTCTAGTCGGCGCGAGAAAGGCGATCAGGAAATTAATTACCAGAGGGTACGGGCAAGGC
TGAGAACCGGCACCGTTTACGTTGTTCCTGCAGGTCATCCAATCACCGAGATAGCTTGCACAG
AGGGCCACCTTGAAATCTTGTGGTTTGATATTAATACGAGCGGCAACGAGAGACAATTCCTGG
CAGGAAAGTACAATGTGCTTCAAACGCTGGAGAAGGAGGTCAGGCAGATATCCTTCAACATA
CCACGTGGGGAAGAGCTGGATGAAGTTTTACGGCGGCAAAAGGATCAAGTCATCCTCAGAGG
GCCCCAAATGCAAAGGCGAGACGAGCCAAGGAGCTCTTCTTAGATCCATGCCATCATCGCAG
CTCGCATCATGGACGACAAGACTAGAGTTTCTCCACGTTCACTCTTTAGTATCTACTTAAGAAT
AAGTTATGCATATATGAAGCCCAAAAAATGTGTTCGAAGATGAGCTCCTTTTATCTTAATGAA
TGTATATATGAGTTTCAACAAACCTATCGTTGGGCTCTTCTCTTGCTACTTCAATGACATGGAA
TGCTGATCTT

FIG. 3

STIMAFVSLLTILQAISSCSVALTEPLATVANQGVFPEDHGRGHQRREEEREENPYVFHS
DRFRMRASSDAGEIRALPNFGEASELLEGISKYRVTCIEMRPNTVMLPHYLDATWILYVT
GGRGYIAYVHQNELVKRKLEEGDVFGVPSGHTFYLVNNDDHNSLRITSLLRTVSTMRGEY
EPYYVAGGRNPETVYSAFSDDVLEAAFNTNVIEARTHFPVHIERESYSMANEEQIREMLR
KRGFSAESMSASEHPKPFNLRNQKPDFENDNGRFTRAGPNENPLLDAVDVTAGFGVLNPG
TMTAPSHNTKATSIAIVTQGEGRIEMACPHLGQHGWSSRREKGDQEINYQRVRARLRTGT
VYVVPAGHPITEIACTEGHLEILWFDINTSGNERQFLAGKYNVLQTLEKEVRQISFNIPR
GEELDEVLRRQKDQVILRGPQMQRRDEPRSSS*IHAIIAARIMDDKTRVSPRSLFSIYLR
ISYAYMKPKKCVRR*APFILMNVYMSFNKPIVGLFSCYFNDMEC*S

* indicates potential stop signal

```
                   *        20         *        40         *        60         *        80
          STIMAFASLLIILLAISSCSAALTEPLA3TANPEVFPEDHGRGHRREEREENPYVFHSDRFMRASSDAGEIRALPNFG
L. Pine : STIMAFVSLLTILQAISSCSVALTEPLATVANQGVFPEDHGRGHQRREEREENPYVFHSDRFMRASSDAGEIRALPNFG :  81
P. Glauca : ---MALASLLIILLAISSSSAALTEPLASTANPEVFPEYLGRGRGRREEREENPYVFHSDSFRTRASSEAGEIRALPNFG :  78

*       100         *       120         *       140         *       160
          EASELLEGIRK5RVTCIEM4PNTVMLPHY6DATWILYVTGGRGYIAYVHQNELVKRKLEEGDVFGVPSGHTFYLVNNDDHN
L. Pine : EASELLEGISKYRVTCIEMRPNTVMLPHYLDATWILYVTGGRGYIAYVHQNELVKRKLEEGDVFGVPSGHTFYLVNNDDHN : 162
P. Glauca : EVSELLEGIRKFRVTCIEMKPNTVMLPHYIDATWILYVTRGRGYIAYVHQNELVKRKLEEGDVFGVPSGHTFYLVNNDDHN : 159

*       180         *       200         *       220         *       240
          3LRIASL6RPVST6RGEY2P5YVAGGRNP2TVYSAFSDDVLEAAFNTNVI2AERHFGGHIEGESIIHANEEQIREM6RKRG
L. Pine : SLRITSLLRTVSTMRGEYEPYYVAGGRNPETVYSAFSDDVLEAAFNTNVIEARTHFPVHIERESYSMANEEQIREMLRKRG : 243
P. Glauca : TLRIASLVRPVSTVRGEYQPFYVAGGRNPQTVYSAFSDDVLEAAFNTNVQQLERIFGGHKSG-VIIHANEEQIREMRKRG : 239

*       260         *       280         *       300         *       320
          FSAESMSAPEHPKPFNLRNQKPDFENDNGRFTIAGPKENPFLDA6DV3AGFADLNPG3MTAPSHN3KATSIAIVTNGEGRI
L. Pine : FSAESMSASEHPKPFNLRNQKPDFENDNGRFTIAGPNENPLLDAVDVTAGFGVLNPGTMTAPSHNTKATSIAIVTQGEGRI : 324
P. Glauca : FSAGSMSAPEHPKPFNLRNQKPDFENENGRFTIAGPKNYPFLDALDVSVGLADLNPGSMTAPSLNSKSTSIGIVTNGEGRI : 320

*       340         *       360         *       380         *       400
          EMACPHLGQHGWSSPRE4GDQDINYQRVRA4LRTG3VY6VPAGHPITEIACTEGHL2IILWFD6NTRGNERKFLAGKNNVLN
L. Pine : EMACPHLGQHGWSSRREKGDQEINYQRVRARLRTGTVVVPAGHPITEIACTEGHLEILWFDINTSGNERQFLAGKYNVLQ : 405
P. Glauca : EMACPHLGQHGWSSPRERGDQDITYQRVWAKLRTGSVIVPAGHPITEIASTNSRLQILWFDLNTRGNERQFLAGKNNVLN : 401

*       420         *       440         *
          TLE4E6RQ6SFN6PRGEE6DEVLQAQKDQVILRGPQMQRRDEARSS
L. Pine : TLEKEVRQISFNIPRGEELDEVLRRQKDQVILRGPQMQRRDEPRSS : 451
P. Glauca : TLEREIRQLSFNVPRGEEIEEVLQAQKDQVILRGPQRRSRDEARSS : 447

```
                 *           20          *          40           *          60          *          80           *          100         *          120
         AAGCA CATCATGGCTTT G TTCTTACTTA CATTCTTC    GCAATTCCTCCT CTC G TGC CTCACTCGAGCCACTAGCCA         GGCCAATC AG AGTTTTCCTGAA ATC    GG CGAGG
L.Pine :  AAAGCACCATCATGGCTTTGGTTTGTTCTTACTTACATTCTTCAACATTCTTCAACTTCCTCCTGTTCCTCCGTTCCTGCCCTCCGGCTCACTGAGCCAGCCACTAGCCACTGTGGCCAATCAAGGAGTTTTCCTGAAGATCATGGGCGAGG
P.Glauca: CAAGCATCATCATGGCTTTGCTTCTTACTTACATTCTTCCTTACTTACATTCTTCAACATTCCTCCCTCCTCCCTCCTCGGCTGCCCTCACTGAGCCAGCAGCCACTAGCCACTGCCCAGCACGGCCAATCCAGAAGTTTTTCCTGAATATCTCGGCCGAGG

*          140          *          160          *          180          *          200          *          220          *          260
         C      GAGACCAGAGAAGA CCGACGAGAGAATCC TA GTATTCCACAGTGACAG TTC GGA    AGAGC TCATCTGA GCTGGTGAAATCAGAGCTT CC AACTTGG GAGG CTCTGAACTT
L.Pine :  GCACCAGAGACGAGAAGAAGAAGAAGAAGACCGACGAGAGAATCGTACGTATTCCACAGTGACAGATTCAGAGATGAGAGCGTCATCGACGTCATCTGACGCTGGTGAAATCAGAGCTTCCCAACTTGGTGAGGCCTCTGAACTT
P.Glauca: CCGAGGGAGACGAGAAGAAGAAGAAGACCGAGCAGAATCCATAGTATTCCACAGTGACAGATTCAGAGAGCAGCTTCCGACCAGCAGCATCATCGAAGCTGGTGAAATCAGAGCTCTGCCGAACTTTGGGGAGGCTCTGAACTT

*          280          *          300          *          320          *          340          *          360          *          380
         CTTGAAGGGATTAG AAAT CAGAGTTACCTGAATGA ACCCAA ACGGT ATGCCTCCCTTCACTAT TTGA GCGACATGGAT TTATATGTTACT GAGGAAGAGGTTACATAGC TA GTGC
L.Pine :  CTTGAAGGGATTAGTAATACAGAGTTACCTGCATGCATTGAATGAAAATGAGAACGTGACCCACACCGTATGCCTCCTCCCTCACTCTGACCGACATGGATTTATATGTTACTGGAGGAAGAAGCTGAAGAAGAGGTTACATAGCTTACGTCC
P.Glauca: CTTGAAGGGATTAGAAAATCAGAGTTACTGCATGCATTGAATGAAAATGAAAATGAAACCCAATGCCCAATACGGTGATGCCTCCCTCACTATATTGACGTGACATGGATTTATATGTGTACTAGGAGGAGAGGTTACATAGCCTATGCC

*          400          *          420          *          440          *          460          *          480          *          520
         ACCAGAATGA CTGGT AAAAGAAAGTTGAGGAAGGAGATGTATT GGTGTTCCAAGTGGTCATACATTTATCTCGT TAACACGATGACCA AACA CCTTCGCAATT C AGTCTC TGGCT C GT
L.Pine :  ACCAGAATGACTGTGAAAAGAAAGTTGAGGAAGAAGTTGGAGGAGAGATGTATTGTGTTCAAGTGTCATACATTTATCTCGTTAACACGATGACCACACAACAGCCTTCGCATTACCAGTCTCCTGCCTACAGT
P.Glauca: ACCAGAATGACTGGTAAAAGAAAGTTGGAGGAAGGAGATGTATTGGTGTTCCAAGTGGTCATACATTTATCTCGTTAACACGATGATGACCATGAAGCTCCAGTCTGCCATTACCCCTTCGCAGTGCTGTCCGT

*          540          *          560          *          580          *          600          *          620          *          640
         GTCTACG T CGAGGAGAATAT AGCCCT CTACGTTG CCGGAGTCGGAATCCT CTACGTTG GAGGTCGGAGTCGGAATCCT AGACTGTTTACTCTGCCTTAGCGATGATGTTCTCGA GCTGCATTCAATACGAACGT A AG AGT GAAC
L.Pine :  GTCTACGATCGAGGAGAATCGAGCCCCTACTACCTTGCCTGCCTACGTTGCGGGGAGGTCGGAGTCGGAATCCTCTACGTTGGATGATGTCGAGACGTGTTCACTCAGACTGTTTCCTGCCTTAGCGATGATGATGTCTCGAAGCTGCATTCAATACCAACGTTATAGAAGCTAGAACA
P.Glauca: GTCTACGGTCCGAGCAGAATATCAGCCCCTTCAGTTGCGGTGCGGAGTCGGAGTCGGAGTCGGAATCCTCTACGTTGGATCGAGTTCTCAGAGTTTCCCGAGCGTGCGAGGCTCCATTGCATTCAATACCAACGT-ACAGCAGGTTGACGACG

*          660          *          680          *          700          *          720          *          740          *          760          *          780
         ATTTTC GCTG ACA A AA GGAGTCATA TCCA G CAAATGAAGAACGATTAGAGAATG TGAGGAAACGGGATTTTCAGCAG CTCAGCACCC CTCAGCACCC AAGCCTTT AACC
L.Pine :  CATTTTCCCGTGCACATAGAACCGGAGTCATATATCCGCATGGCAAATGAAATGAACAACAGATTAGAGAATTTCAGGAAAAATTGTCAGGAAACGGGAAAATCGGGAGTTTCAGCAGGATCAGCCACCATGTCTGCATCGCAGGATCATGTCACCTTCACC
P.Glauca: TATTTTC-GGTGGACACAAAAGTGCAGTCAATCCACG-CAAATGAAGAACGATTAGAGAATGATGAGGAAGAACGGGATTTTCAGCCAGGATCATGTCCAGCAGATCTATGTCCACCTGAGCGCTCCAAGCCTTTCACC

*          800          *          820          *          840          *          860          *          880          *          900
         TTCGAACCAGAAGCCAGATTCAGAACGA AATGGCAGGTTTACTA GCTGGTCCGA A ATCCT TTCT GACGCG TCGA GTT CTG TGGG TTG CG TTGAATCCTGA CCATGAC
L.Pine :  CATTTTCCCGTGCACATAGAACCGGAGTCATATATCCGCATGGCAAATGAAATGAACAACAGATTAGAGAATTTCAGGAAAAATTGTCAGGAAACGGGAAAATCGGGAGTTTCAGCAGGATCAGCCACCATGTCTGCATCGCAGGATCATGTCACCTTCACC
P.Glauca: TTCGAACCAGAAGCCAGATTCAGAACGAAAATGGCAGGTTTACTAGAGCTGGTCCGAAATCCTTCTTTTCTAGACGCCGTCGAGTTCTGTGGGTTGCGTTTGAATCCTGAACCATGAC
```

FIG. 5B

```
                   920           *           940           *           960           *           980           *          1000           *          1020           *          1040
                    AGCCCCATCTC CAAC CGAAA CAAC TCAATCG CATTGT AC  A GGGGA GGAAGGATTGAGATGGCGTGCCCGCACCTTGGTCGTCAACATCG TGGTCTAGTC GCGCGAGA AGGCGA CA GA
L.Pine   :          AGCCCCATCTCCAACACGAAAGCAACCACCTCAATCGCATTGTCACACAGGGGAGGGGAGGAAGGATTGAGATGGCGTGCCCGCACCTTGGTCGTCAACATGGTCTAGTCGGCGCGAGAAAGGCGATCAGGAA
P.Glauca :          AGCCCCATCTCAACTGCAAATCAATCGCAATGCATTGTTACCGGCATTGTTGCGAATGGGAATGGGAAGGAAGGATTGAGATGGAGTGCCCGACCTTGGTCGTCAACATGGTCAACATGTCAACATGTCAACATGTTGGTCTAGTCCCGGCGAGAGAGCGACCAAGAT
                                 *          1060           *          1080           *          1100           *          1120           *          1140           *          1160           *
                    ATTA TACCAGAG GT GGGCCAA GCTGAG ACCGGCA CGTTTA TTGTTCCTGC GGTCATCCAATCACCGAGATAGCTT ACA A GCC CCT AAATCTTGTGGTTGAT TTAATAC
L.Pine   :          ATTAATTACCAGAGGGTACGGGCAAGGCTGAGAACCGGCACCGTTTACGTTGTTCCTGCAGGTCATCATCCAATCACCGAGATAGCTTCCACAGAGGGCCACCTTGAAATCTTGTGGTTGATTATTAATACGA
P.Glauca :          ATTACCTACCAGAGAGTCTGGGCAAGCTGAGGCTGAGAAGCTGAGAACCAATGCTTATATGTCCTGCCGCGTTCATCCAATCACCCGAGATAGCTTCAACATAGCTTCAACAACAGCCCGCCTACGCCGTCGCAAATCTGTCGTTGATCTTAATACCC
                                 *          1180           *          1200           *          1220           *          1240           *          1260           *          1280           *
                    GCGGCAACGAGAGACAATTCCTGGCCAGGAAAG ACAATGTGCTT A ACG TGGAGA GGAG TCAGGCAG TATCCTTCAAC TACCACGTGGGGAAGAG T GA GAAGT TT C G GCAAAAGGA
L.Pine   :          GCGGGCAACGAGAGAGACAATTCCTCGGCAGGAAAGTACAATGCTTCTTCAAACGCTGCAGCCGTTGAACATGTGCTTAACACGTTGGACACGTTGGAGATTGAGAAGAGTTTACCGGCGAAAGGAA
P.Glauca :          GCGGCAACGAGACAATTCCTGGCAGGAGAACAATGTGCTTCAACACGTTGCAACACGTTGGGAGATCAGGCAGCAGCTACAGCAGCTACAGCAGCAGCTGGGAGGGAGAATTGAAGAGAGTTGCAGGCGCAAAAGGA
                                 *          1340           *          1360           *          1380           *          1400           *          1420           *
                    TCAAGTCATCCT AGAGC CCCCA   C AAG CG GACCAG  C AGGAGCCTTCTTCTTAGATCCAG CATCATCCAC TCGCAT ATGGACGACA GAC AGAGTTTCTC ACGTTCACTCTT A T
L.Pine   :          TCAAGTCATCCTCAGAGGGGCCCAAATGCAAAGGCGAGACGAGCCAAGGAGCCAGAGCCTCTCTTCTTAGATCCATCATCCAGCTCGCAGCTGCAGCCTGAGCCAGCCAGTCATCATGGACGAGATGACAGAGTCGAGCTTTCTCCCAGCCACACTCTTGAT
P.Glauca :          TCAAGTCATCCTGAGAGGGCCCCAACGAACGGAAGCCGGACGAGGCGAGGCGAGGCGAGGAGCTCTTCTTAGATCCAGATCCAGATCCATCATCCAGATCCAGATCATGACAGCAAGACAAGAGTTCACTGTTAGT
                                 *          1440           *          1460           *          1480           *          1500           *          1520           *          1540           *          1560
                    ATCTACTTAA AATAAG TAT CATATATGAAGCCCAA AAATGTGTTCGAAGATGA CTC TT T TCT AATGAATGTAT T AACAA CTATCCTGGCTTCTCCTCTGCTACTTCA
L.Pine   :          ATCTACTTAAGAATAAGTATGCATATATGAAGCCCAAAAAAAATGTGTTCGAAGATGAGCTCCTTTATCTTAATGAATGAGCTCCTTTTATCTTAATGAATGATATGAGTTCAACAACCTATCGTTGGCTCTTCTTCTCTTGCTACTTCA
P.Glauca :          ATCTACTTAATAAAATAAGCTATCCATATATGAAGCCCAATATAAATGTGTTCAAGATGAACTCTTTGTCTAAATGAATGTATGAGTCT-AACAAAGCTATCGTTGGCTCTTCTTGGCTCTTCTTGCTACTTCA
                                 *          1580
                    ATGA AATGGAAGC GATCTT
L.Pine   :          ATGACATGGAATGCTGATCTT--------
P.Glauca :          ATGAAATGGAATGCAGATCTTCCTTCCTTAAAAAAAAA
```

FIG. 11

ACTATAGGGCACGCGTGGTCGACGGCCCGGGCTGGTAAAAATTCATTTAC
TAATCAAAACATGATGAGATTCATAACCAAAGTCTGTTATAAACCATGAT
TATAACCAACAGATTAACAATGATAGAACAACCATTAAAACCACATAATA
ACAAGTACATTTACACATGGAACACAAGAGGAAAATAGCTCTTATTAACA
TATGAAAAATGTAACTAGGTCAAGGACTTCCACGCACCAACCAACCATAG
ATTGGGCTGAACCAAATCTTTCTTTCAACTAATCACCCCTAAGCCATATT
CCCAGCATGAATGTGGGACTTACAAAAAAACAAACAAGGATTCCTTAGGA
TTTACCATAATCCACCAAGGGATTCCTAGGCCCAAGCCCTCATCTATACA
ACTAGGATTTACTGCAATCCCACCAAGGGATTCCTAAGCCCAAACAAGAA
ACACACACTACCAGGATTTAGATAAACCCCCTTTGTGGNGCTGCTATCAG
CTNNGTTTCTTTTACCTTCTGNATATCTTCTGNGGACACCTGNCTTTANA
AGCCGATTCCACCNT

VICILIN-LIKE SEED STORAGE PROTEIN GENE PROMOTER AND METHODS OF USING THE SAME

FIELD OF THE INVENTION

The present invention relates to isolated vicilin-like gene promoters, promoter-gene constructs, methods of producing polypeptides in plants, methods of monitoring embryo maturity of conifers, and plants per se.

BACKGROUND OF THE INVENTION

The expression of seed-storage protein ("SSP") genes in plants is induced during seed development and is restricted to the embryos. SSP gene expression takes place primarily in specialized storage cells located in the embryonic axis, cotyledons, and the endosperm of developing seeds (Goldberg et al., Cell, 56:149–160, 1989). Notably, SSP gene expression does not take place in mature vegetative organs (Thomas, Plant Cell, 5:1401–1410, 1993). In angiosperms and gymnosperms, maximum accumulation of seed-storage proteins and abundant synthesis of oil and starch have been observed during mid to late embryo development.

One example of SSP gene expression is the synthesis of the 2S protein, a seed storage protein encoded by a multi-gene family which synthesis has been shown to be limited to the later stages of seed development. The expression of the 2S protein has been correlated with the accumulation of 2S mRNA (Gander et al., Plant Mol. Biol., 16:437–448, 1991). Regulatory domains within plant promoters found to be necessary for specific expression patterns of SSPs have been determined using deletion and gain of function experiments in transgenic plants (da Silva et al., Plant J., 5:493–505, 1994; de Parter et al., Plant Cell, 5:877–886, 1993; Kawagoe et al., Plant J., 5:885–890,1994; Lessard et al., Plant Mol. Biol., 22:873–885, 1993; Thomas et al., Plant Cell, 2:1171–1180, 1990). Genes that regulate expression of SSPs represent an important model for the study of the mechanisms of developmental-stage and tissue-specific gene expression.

The gene families that encode the main SSPs have been characterized in several plant species (Guerche et al., Plant Cell, 2:469–478, 1990; Higgins, Ann. Rev. Plant Physiol., 35:191–221,1984;Panget al., Plant Mol. Biol., 11:805–820, 1988). Seed-storage proteins have been classified into four different groups based on solubility. Albumins, which are water-soluble; globulins, which are salt-soluble; glutelins, which are soluble in acids, alkali ionic detergents, and urea-containing solutions; and prolamins, which are alcohol soluble. The glutelins and prolamins are the major forms of cereal SSPs while the globulins are the most prevalent class of SSPs in legumes and oats (Shotwell et al., The Biochemistry of Plants, Vol. 15: A Comprehensive Treatise, Academic Press, San Diego, Calif., pages 297–345, 1989; Krochko et al., Plant Physiology, 99:46–53, 1992). However, to date there has been no detailed study of the accumulation of seed-storage proteins and the qualitative and quantitative properties of seed-storage proteins in the majority of angiosperms and gymnosperms.

A recent study showed a marked time differential between SSP synthesis and mRNA accumulation during development of zygotic and somatic embryos of alfalfa (Medicago sativa L.). Of three storage proteins studied (7S, 11S, and 2S), mRNA for the 2S protein was found early in somatic embryo development (day 3) but the protein associated with the 2S message was not evident until later (day 10). Thus, both transcriptional and post-transcriptional events appear to be important in determining the protein complement of seed tissues. (Krochko et al., 1992).

Superficially, somatic embryos mimic the developmental stages of zygotic seeds, i.e., the globular, heart, torpedo, and cotyledonary stages (Steward et al., Science, 143:20–27, 1964). However, despite the gross morphological similarities, somatic embryos may exhibit other features which suggest aberrant development, including truncated cotyledonary development, precocious germination, recallusing, multiple or fuse cotyledons, or inability to germinate (Ammirato, Bio/Technology, 1:68–74, 1983; Bapat et al., Plant Cell Rep., 7:538–541, 1988).

Comparisons between somatic and zygotic embryos have shown that somatic embryos can accumulate SSPs (Crouch, Planta, 156:64–74, 1982; Shoemaker et al., Plant Cell Rep., 6:12–15, 1987), and can also be induced to become desiccation tolerant under appropriate culture conditions (Senaratna et al., Plant Sci., 65:253–259, 1989). However, few studies have been conducted on physiological and biochemical changes occurring in somatic embryogenesis in parallel with studies in zygotic embryogenesis. In particular, seed-specific storage proteins, because of their nature and abundance, are expected to be useful markers in the study of gene expression in embryogenic systems.

SSP accumulation is thought to be temporally and spatially regulated, primarily at the level of gene transcription (Muntz, Biochem. Physiol. Pflnazen, 182:93–116, 1987). This conclusion is based primarily on the absence of SSP mRNA in non-seed tissues, and the observed coincidence between the period of maximum seed storage protein synthesis in developing seeds and mRNA accumulation, as determined by Northern blot (Walling et al., Proc. Natl. Acad. Sci. USA, 83:2123–2127, 1986). Factors which affect the accumulation of SSPs in somatic and zygotic embryos vary with the specific SSP, the developmental stage, the tissue (axis or cotyledon), and nutritional conditions (Muntz, Biochem. Physiol. Pflnazen, 182:93–116, 1987; Walling et al., Proc. Natl. Acad. Sci. USA, 83:2123–2127, 1986; Laden et al., Plant Physiol., 84:35–41,1987). The relative magnitude of each of these factors remains to be determined.

Many genes have been introduced into plants using a variety of genetic engineering techniques, sometimes using regulatory elements from sources other than the target plant. Often, the gene coding for the desired polypeptide is placed under the control of a constitutive promoter allowing the expression of the desired polypeptide in the plant throughout the entire life of the plant, irrespective of the plant's developmental stage. For example, the 35S promoter from Cauliflower Mosaic Virus (CaMV) has been used extensively for constitutive expression of heterologous genes.

For some applications, however, it is not necessary to continuously express the desired polypeptide throughout the life of the plant. In these instances, it is desirable to limit the expression of the desired polypeptide to specific instances, often linked to the stage of plant development. It is often useful to control the time when the desired polypeptide is to be expressed through the use of inducers. In some situations, it is desirable to maintain baseline expression of a desired polypeptide while allowing over-expression of the desired polypeptide at certain times.

While current compositions and methods may be effective to deliver certain genes to plants, there is a need for improved compositions and methods. There is a need for an inducible promoter that will allow the expression of a desired polypeptide. There is also a need for a method of transforming a target plant with a DNA construct comprising an inducible promoter operatively linked to one or more genes coding for desired polypeptides. There is a further need for a method of assessing the developmental maturity of plant embryos.

SUMMARY OF THE INVENTION

The present invention is directed to isolated promoters comprising novel nucleic acid sequences. The promoter is a vicilin-like seed storage gene sequence and may be a nucleic acid sequence selected from the group consisting of SEQ ID NO:1, SEQ ID NO: 2, SEQ ID NO:3, SEQ ID NO:4, SEQ ID NO:5 and SEQ ID NO:6. The isolated promoter of the present invention includes a fragment thereof having substantially the same activity.

Another embodiment of the present invention is a construct of the promoter operably linked to a desired gene. Also provided by the present invention is a nucleic acid sequence having the functional properties of the promoter of the present invention, the complement of which hybridizes under stringent conditions to the nucleic acid sequence of the promoter.

The present invention is also directed to methods of expressing a desired polypeptide in a plant, the method comprising preparing a construct of a vicilin-like gene promoter sequence operably linked to a desired gene, thereby producing a promoter-gene construct, and transforming a plant with the promoter-gene construct which thereby ultimately expresses a desired polypeptide in the plant. Typically, the polypeptide is a SSP or a structural protein. The desired gene may heterologous or non-heterologous and may be a reporter gene, according to the present invention. The method of expressing a desired polypeptide may include constitutive or induced expression of the desired gene. Suitable inducers include abscisic acid (ABA), heat, and light.

Yet another embodiment of the present invention is a method of monitoring embryo development in conifers, the method comprising preparing a construct of a vicilin-like gene promoter sequence operably linked to a reporter gene, thereby producing a promoter-gene construct; and transforming an embryo with the construct, wherein the expression of the reporter gene is indicative of the degree of activation of the vicilin-like gene promoter thereby providing a qualitative marker of embryo development that may be monitored.

The present invention is also directed to transgenic plants, including transgenic plants comprising a vicilin-like gene promoter operably linked to a desired gene. The plant may be an angiosperm or gymnosperm, preferably a conifer.

BRIEF DESCRIPTION OF THE DRAWINGS

FIG. 1 depicts the alignment of four promoters isolated from loblolly pine (SEQ ID NOS: 1–4) and the predicted consensus sequence (SEQ ID NO:6) of SEQ ID NOS: 1–4.

FIG. 2 depicts the sequence of vicilin cDNA (SEQ ID NO:16) from loblolly pine. Initiator and termination codons are marked in bold. A polyadenylation-like sequence in the 3'untranslated region is also marked in bold.

FIG. 3 depicts the loblolly pine vicilin-like SSP amino acid sequence (SEQ ID NO:17).

FIG. 4 depicts the amino acid alignment of vicilin-like proteins from loblolly pine (SEQ ID NO:17) and *Picea glauca* (SEQ ID NO:18), as well as the predicted consensus sequence.

FIG. 5 depicts the alignment of Loblolly pine vicilin-like cDNA (SEQ ID NO: 16) and *Picea glauca* vicilin-like cDNA. (SEQ ID NO:7)

FIG. 11 depicts the sequence of a fifth promoter (SEQ ID NO:5) isolated from loblolly pine.

DESCRIPTION OF PREFERRED EMBODIMENTS

Figure 6:
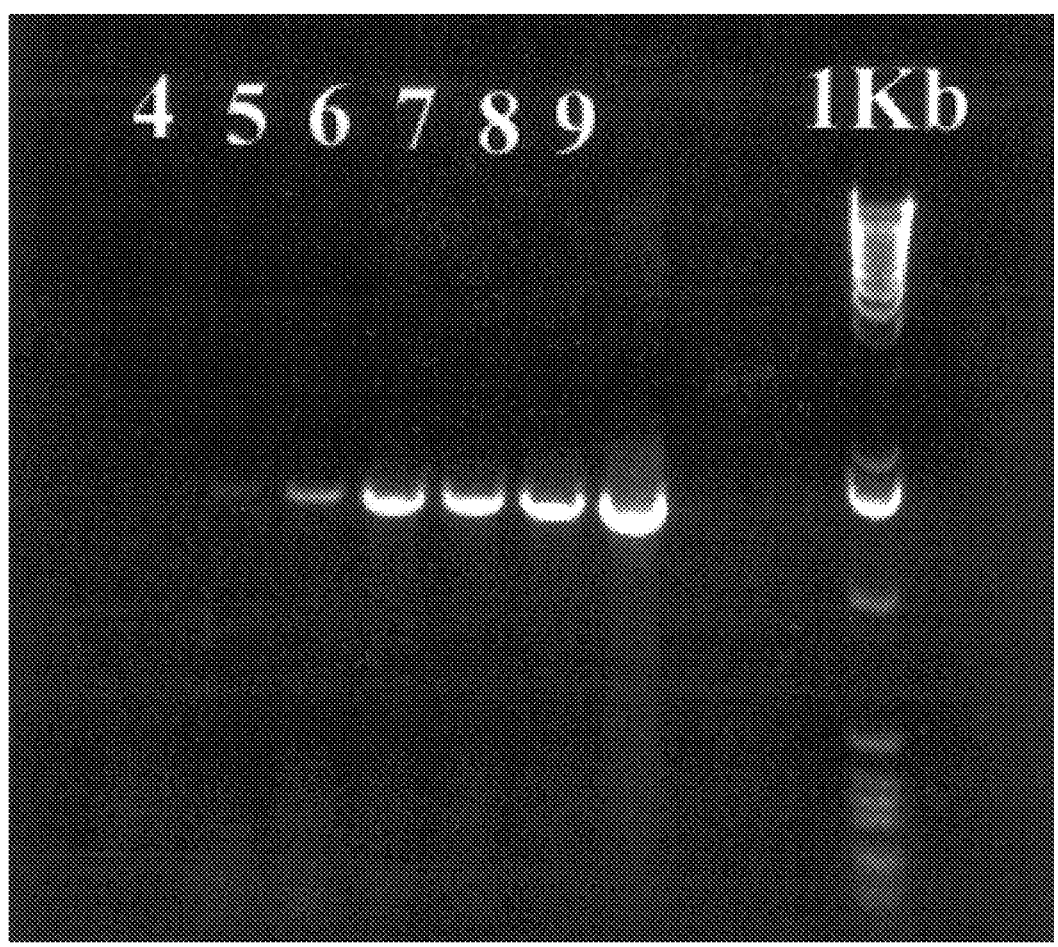
FIG. 6 depicts a gel showing the presence of vicilin gene transcripts in different stages of somatic embryogenesis. Lanes 4–9 represent stages 4–9, respectively.
Figure 7:
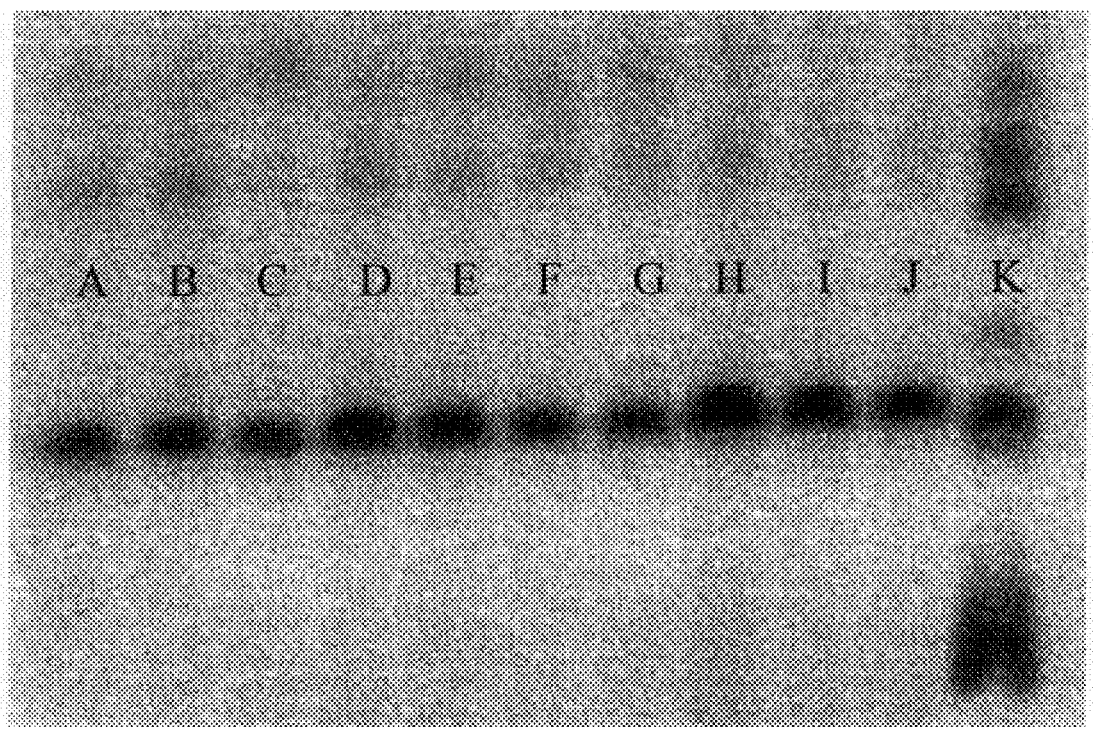
FIG. 7 depicts vicilin gene expression in late zygotic embryos. An RT-PCR reaction was carried out with vicilin primers, which produced 1.4 Kb fragments of the vicilin gene. Columns A-J represent stages 9.1–9.10, respectively. Column K represents a 1 Kb ladder.
Figure 8:
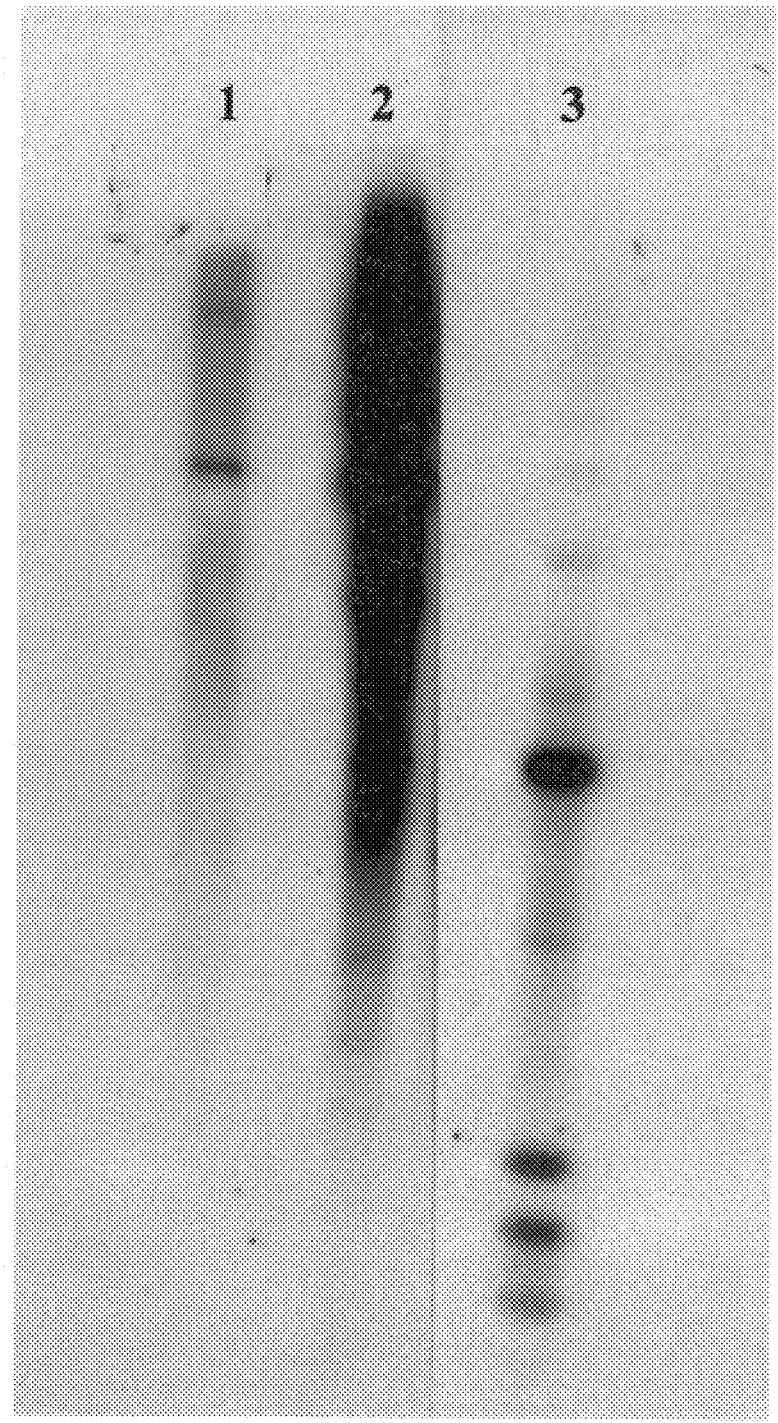
FIG. 8 depicts a Southern blot hybridization with the vicilin gene. Lane 1 represents tomato genomic DNA. Lane 2 represents Loblolly pine genomic DNA. Lane 3 represents a 1 Kb ladder marker.
Figure 9A:
FIG. 9A depicts the effect of heat as an inducer on vicilin gene expression.
Figure 9B:
FIG. 9B depicts the efficiency of transfer from the gel to the blotting media.
Figure 10:
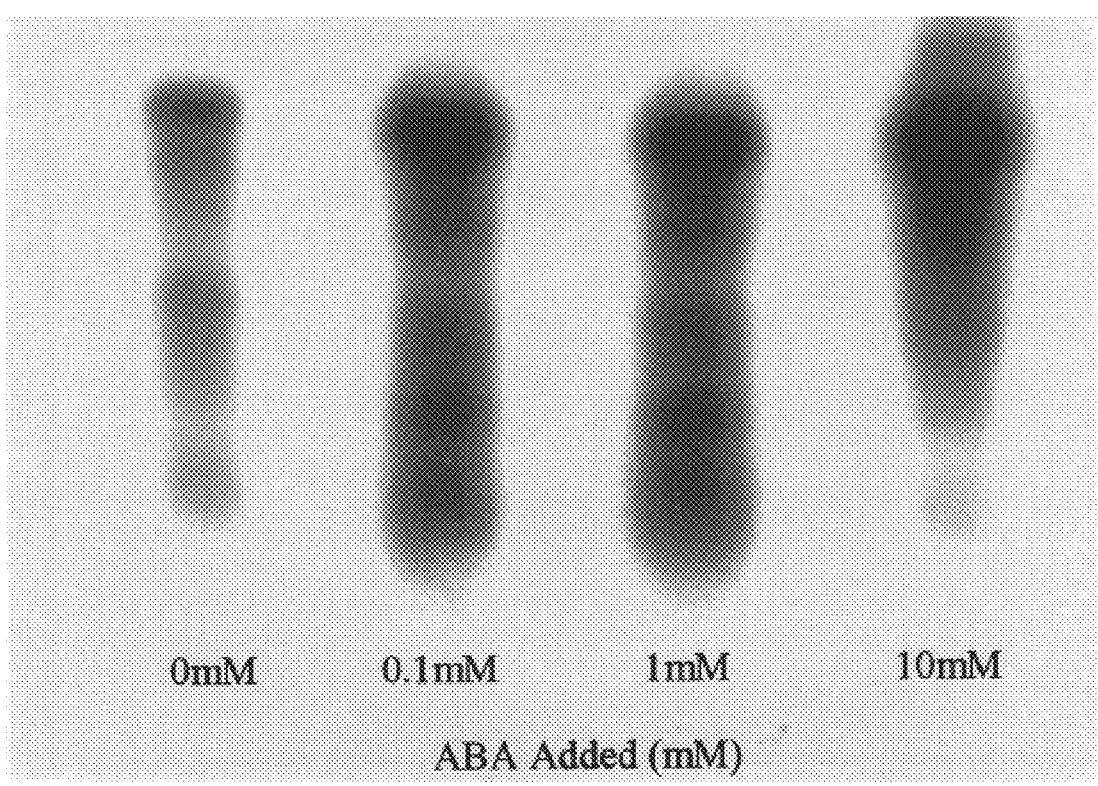
FIG. 10 depicts the effect of different concentrations of ABA as an inducer of vicilin gene expression. From left to right, 0.0 $\mu$M, 0.1 $\mu$M, 1.0 $\mu$M, and 10.0 $\mu$M ABA were added to the samples.

The present invention is directed to vicilin-like gene promoters including nucleic acid sequences thereof. The vicilin-like gene promoters were isolated from Loblolly pine genes encoding vicilin-like SSPs. As used herein, the term "vicilin-like" refers to proteins (and polypeptide sequences and nucleic acids encoding therefor) that are SSPs substantially similar to the SSPs found associated with the seeds of leguminous plants. Similarly, vicilin-like promoters are promoters of genes encoding the above mentioned proteins.

As used herein, the term "promoter" refers to a nucleic acid sequence that directs the transcription of a gene. Typically, a promoter is located in the 5'region of a gene and is proximal to the transcriptional start site of the gene. Promoters of the present invention are from about 100 to about 600 nucleotides in length. In a preferred embodiment, the promoters are from about 200 to about 400 nucleotides in length. In a more preferred embodiment, promoters are about 340 nucleotides in length. The present invention includes six vicilin-like gene promoter sequences, including SEQ ID NO:1, SEQ ID NO:2, SEQ ID NO:3, SEQ ID NO:4, SEQ ID NO:5, and a predicted consensus sequence of SEQ ID NOS: 1–4, SEQ ID NO:6.

All or part of the vicilin-like promoter may be used to express a sequence or gene in accordance with the present invention. All or part of the vicilin-like promoter may be operably linked with a nucleic acid sequence or gene encoding a protein to direct the expression of the sequence or gene. A portion, a part, a fragment, or the like, refers to one or more groups of nucleic acids within the vicilin-like promoter which control the expression of sequences that are operably linked to the promoter. "All", "part", and nucleic acid sequences which are "substantially similar" to the nucleic acid sequence of the vicilin-like promoter, for purposes of the present invention, means a nucleic acid molecule the sequence of which is preferably 25%, preferably 50%, more preferably 75%, and most preferably 100% identical to that of the vicilin-like promoter. The portion of the vicilin-like promoter sequence may be in a single consecutive arrangement, or more than one arrangement of consecutive nucleic acids. In addition, the present invention includes sequences which are substantially similar to the sequences of SEQ ID NOS: 1, 2, 3, 4, 5, 6, or portions thereof. Substantially similar, for purposes of the present invention is a sequence which is preferably 25%, preferably 50%, more preferably 75%, and most preferably 100% identical to SEQ ID NO:1, 2, 3, 4, 5, or 6. All or part of SEQ ID NOS: 1, 2, 3, 4, 5, or 6 may be used to express a sequence or gene operably linked thereto.

The vicilin-like gene promoter may be a functional equivalent of any of the nucleic acid sequences set forth in SEQ ID NOS: 1, 2, 3, 4, 5, or 6. As used herein, the term "functional equivalent" refers to any nucleic acid sequence which is complementary to a reference nucleic acid sequence which, under stringent conditions, will hybridize with the reference sequence and has activity similar to the vicilin-like gene promoter.

As used herein, the term "stringent hybridization conditions" are those in which hybridization takes place at 65° C. in 2.5×saline citrate buffer (SSC) followed by a rinse step at 37° C. in a reduced buffer concentration.

As used herein, the term "percent homology" relates to the ratio of the identical nucleotides when two sequences are compared to the total number of nucleotides when the sequences are aligned. Sequence alignments for both DNA and proteins were performed using the National Center for Biotechnology Information's BLAST utility program using default settings.

Other embodiments of the present invention are constructs which include, but are not limited to, nucleic acid sequences including DNA, cDNA, genomic DNA, RNA, mRNA, tRNA, suitable nucleic acid sequences such as the sequences set forth in SEQ ID NOS: 1, 2, 3, 4, 5, 6, and conservative alterations in such nucleic acid sequences including additions, deletions, mutations, and homologues. The sequences within the scope of the present invention include antisense sequences which may alter plant characteristics, including those identified above. Antisense sequences may prevent the translation of certain sequences in plants. Inhibition of expression of certain sequences, such as those responsible for the characteristics identified herein, may be achieved with antisense sequences.

As used herein, the term "desired gene" refers to a nucleic acid sequence which encodes a desired polypeptide. According to the instant invention, "desired genes" include, but are not limited to, SSP genes, structural genes, insecticidal toxins, herbicide resistance genes, drought tolerance genes, anti-microbial genes, anti-fungal genes, anti-viral genes, genes encoding regulatory proteins, and genes encoding enzymes involved in metabolic pathways. While the term "gene" is used throughout the specification to define the sequence operably linked to a vicilin-like promoter, "gene" includes any sequence that has substantially the same activity as the desired gene. One measure of "substantially the same activity", for example, is a functioning polypeptide or protein resulting from a nucleic acid sequence operably linked to a vicilin-like promoter of the present invention. Accordingly, all or part of a gene is included in the definition of "desired gene". The definitions set forth above to describe all or part of the vicilin-like promoter are applicable to a desired gene as well. The desired genes may be heterologous or non-heterologous.

As used herein, the term "polypeptide" refers to any translation product of a nucleic acid molecule, regardless of size, whether or not glycosylated, phosphorylated or modified post-translationally. Examples of "polypeptides" contemplated by the instant invention include amino acids, proteins and peptides. "Desired polypeptides" refer to polypeptides encoded by a desired gene, and that may be the result of a promoter-gene construct of the present invention, including polypeptides that are functionally equivalent or that are fragments of the polypeptides or selected polypeptides.

According to the present invention, methods of expressing polypeptides in a plant are provided. Such methods comprise constructing an expression vector construct comprising a vicilin-like gene promoter operably linked to a desired gene and administering the construct to the plant. At least one gene encoding a desired polypeptide may be administered to a plant; however, more than one gene encoding desired polypeptides may be administered to a plant in accordance with the methods of the present invention. The nucleic acid sequence that encodes the polypeptide is operably linked to regulatory elements e.g., a vicilin-like gene promoter) necessary for expression of the sequence in the plant.

As used herein, the term "administration" refers to the mechanism of supplying the expression vector comprising a vicilin-like gene promoter and at least one desired gene to a target plant. Methods of administration of expression vectors to plants are known to those of skill in the art. According to some embodiments of the invention, the expression vector is administered to the target plant by infection with Agrobacterium. One method known in the art for administering the expression vector to a plant is the use of a gene gun. Electroporation and microinjection may also be used to introduce expression vectors into the target plant.

Administration to a plant may comprise transforming the plant with the promoter-gene construct. An expression vector, comprising a vicilin-like gene promoter operably linked to at least one desired gene, may be used to achieve transformation of a plant. As used herein, the term "expression vector" refers to the molecules that comprise a nucleic acid sequence which encode one or more desired polypeptides and which include initiation and termination signals operably linked to regulatory elements including a promoter and polyadenylation signal capable of directing expression in the plant to be treated. Initiation codons and stop codons are generally considered to be part of a nucleic acid sequence that encodes a polypeptide. However, it is necessary that these elements be functional in the cells of the plant to which the gene construct is administered, e.g., the initiation and termination codons are in frame with the coding sequence. Administration to the desired plant may be performed in conjunction with agents which facilitate the uptake and/or expression of the desired gene by the target plant. Such agents include but are not limited to polyethylene glycol, heat treatment of cells, and cold treatment of cells.

Desired genes within expression vectors administered to a plant embryo are expressed under control of the vicilin-like gene promoter, producing the desired polypeptide. Typical expression vectors include, but are not limited to, the pBl series of vectors and derivatives thereof, and green fluorescent protein reporter systems. Other methods of delivering sequences into plants are known in the art, including and not limited to Ti-plasmid vectors, in vitro protoplast transformation, plant virus-mediated transformation, liposome-mediated transformation, gene gun, and ballistic particles.

Target plants to be used in accordance with the present invention are all species of higher and lower plants of the Plant Kingdom. Plant embryos, seedlings, and seeds are included in the scope of the invention. The vicilin-like promoter-gene constructs are useful in plants, plant parts, seeds, and plant culture. A mature plant includes a plant at any stage in development beyond the seedling. A seedling is a very young, immature plant in the early stages of development.

The present invention contemplates target plants including, but not limited to, gymnosperms including and not limited to conifers such as evergreens, trees and shrubs, cycads, oaks, gumwoods, aspens, cottonwoods; angiosperms including but not limited to, annuals, perennials, monocotyledons, and dicotyledons; and the like.

A further aspect of the methods of expressing a desired polypeptide in a plant optionally includes inducing expression of the desired gene with a suitable inducer. The vicilin-like gene promoter is induced by an agent, i.e., an inducer, that initiates transcription, or increases the rate of transcription, of a desired gene. Inducers contemplated by the instant invention include, but are not limited to, abscisic acid, heat, light, and other endogenous signals. Abscisic acid, in accordance with the present invention, includes amounts of abscisic acid not typically found in plants in under natural conditions. For example, in loblolly pine, abscisic acid from about 0.001 $\mu$M to about 10 $\mu$M can be used as an inducer. Heat, in accordance with the present invention, includes temperatures not typically existing for plants growing under natural conditions. For example, in loblolly pine, heat, from about 30° C. to about 50° C. can be used as an inducer.

Yet another embodiment of the instant invention provides a method of monitoring embryo development in plants, including, but not limited to conifers. The methods of monitoring embryo development include assessing the maturity of seed embryos. One embodiment of the method comprises administering to a target plant a vicilin-like gene promoter operably linked to at least one reporter gene, and transforming an embryo with that construct. Upon uptake by the target plant, the plant's cells express the reporter gene. The expression of the reporter gene under the control of the vicilin-like gene promoter is indicative of the degree of activation of the vicilin-like gene promoter and thereby provides a quantitative marker of embryo development that may be monitored.

As used herein, the term "reporter gene" refers to genes and polypeptides encoded thereby, that are used to monitor gene expression, and, in some cases to allow protein localization in cells. Reporter genes include, but are not limited to, green fluorescent protein (GFP), alkaline phosphatase, chloramphenicol acetyltransferase, B-glucuronidase (GUS), firefly luciferase, bacterial luciferase and β-galactosidase. In a preferred embodiment, the reporter gene encodes GUS. In a more preferred embodiment, the reporter gene encodes green fluorescent protein.

The stage of development of a conifer or other plant embryo can be evaluated by monitoring the expression of a reporter gene functionally linked to a promoter. A non-limiting example of such a promoter is the vicilin-like gene promoter. The reporter gene will only be expressed when the vicilin-like promoter is induced, an event that is coupled to, and therefore an indicator of the maturity of the embryo. The appearance of an easily assayable phenotype, characteristic of the reporter protein, such as color production in an assay, fluorescence of embryos, or the ability of an embryo to grow in the presence of a particular chemical, is dependent on expression of the reporter gene, which is in turn controlled by the vicilin-like promoter in such transgenic embryos. Such phenotypic changes provides a means to assay for embryos having reached a particular stage of development.

Also embodied by the present invention is a "transgenic plant" that refers to a target plant comprising one or more constructs of a vicilin-like gene promoter linked to a desired gene.

Depending upon the nature of the polypeptide produced according to the instant invention, various aspects of the present invention, such as those set forth below, can be exploited. For example, if the polypeptide encoded by the desired gene is a reporter gene, the expression of the polypeptide in the desired plant provides methods of assessing promoter activity. If the polypeptide encoded by the desired gene is a SSP, the expression of the polypeptide provides increased amounts of SSP.

The following examples are meant to illustrate the invention and are not intended to limit the scope of the invention in any way. Those skilled in the art will recognize modifications that are within the spirit and scope of the invention. All references cited herein are hereby incorporated by reference in their entirety.

EXAMPLES

Example 1

Cell Cultures, RNA Preparations, and Vicilin-like Genes

Cell suspension culture BC#260, comprising early stage embryos and undifferentiated cell mass, was grown in embryo maintenance media (Medium 16, see Table 1). The culture was subcultured weekly into embryo maturation media (Medium 240, see Table 1) for Loblolly pine embryos (stages one to nine). Both Medium 16 and Medium 240 are described by Pullman et al.(TAPPI R&D Division Biological Sciences Symposium, Oct. 3–6, 1994, Minneapolis, Minn., 31–34).

TABLE 1

Media compositions for liquid maintenance (16), and development and maturation media (240).

| Components (mg/l) | Media 16 | Media 240 |
|---|---|---|
| $NH_4NO_3$ | 603.8 | 200 |
| $KNO_3$ | 909.9 | 909.9 |
| $KH_2PO_4$ | 136.1 | 136.1 |
| $Ca(NO_3)_2.4H_2O$ | 236.2 | 236.2 |
| $MgSO_4.7H_2O$ | 246.5 | 246.5 |
| $Mg(NO_3)_2.6H_2O$ | 256.5 | 256.5 |
| $MgCl_2.6H_2O$ | 101.7 | 101.7 |
| KI | 4.15 | 4.15 |
| $H_3BO_3$ | 15.5 | 15.5 |
| $MnSO_4.H_2O$ | 10.5 | 10.5 |
| $ZnSO_4.7H_2O$ | 14.4 | 14.4 |
| $Na_2MoO_4.2H_2O$ | 0.125 | 0.125 |
| $CuSO_4.5H_2O$ | 0.125 | 0.125 |
| $CoCl_2.6H_2O$ | 0.125 | 0.125 |
| $FeSO_4.7H_2O$ | 6.95 | 13.9 |
| $Na_2EDTA$ | 9.33 | 18.65 |
| Maltose | 0 | 20000 |
| Sucrose | 30000 | 0 |
| PEG 8,000 | 0 | 130000 |
| myo-Inositol | 1000 | 20000 |
| Casamino acids | 500 | 500 |
| L-Glutamine | 450 | 450 |
| Thiamine.HCl | 1 | 1 |
| Pyridoxine.HCl | 0.5 | 0.5 |
| Nicotinic acid | 0.5 | 0.5 |

TABLE 1-continued

Media compositions for liquid maintenance (16),
and development and maturation media (240).

| Components (mg/l) | Media 16 | Media 240 |
|---|---|---|
| Glycine | 2 | 2 |
| 2,4-D | 1.1 | 0 |
| BAP | 0.45 | 0 |
| Kinetin | 0.43 | 0 |
| ABA | 0 | 5.2 |
| Gelrite | 0 | 2500 |
| pH | 5.7 | 5.7 |

Cell suspension culture BC#260 was then treated with 3 different concentrations of abscisic acid (ABA); 0.1 mM, 1 mM, and 10 mM added to the embryo maintenance media. Treatments were over a period of four days. Cultures were incubated at room temperature with constant shaking. Treatment was performed on cells from the end of the seven-day growth cycle (early log phase of cell division.)

A three day old cell suspension culture #BC260 was used for heat treatment. Four equal aliquots, each of 20 mL of cell culture, were grown in a 37° C. shaking incubator for 0, 6, 15 and 15+(drying time) hours. RNA was isolated from each aliquot after each time course.

RNA was isolated using modifications of the methods of Sambrook et al. (*Molecular Cloning, A Laboratory Manual,* Cold Spring Harbor Laboratory Press, NY, 1989) and Krochko et al. (*Plant Physiol.,* 99:46–53, 1992). Cell suspensions and embryos were ground in extraction buffer (45% guanidium HCl, 10 mM EDTA, 2.5% Sarkosyl, 1% β-mercaptoethanol, and 50 mM Tris-HCl (pH 7.6). A ratio of 0.5 mL of extraction buffer to 0.1 g tissue was used. An equal volume of preheated phenol/chloroform/isoamyl alcohol (25:24:1) was added to the homogenate. After centrifugation at 5000 g for 10 minutes at room temperature, the supernatant was collected and extracted with an equal volume of chloroform/isoamyl alcohol (24:1). The RNA was precipitated by adding an equal volume of chilled isopropanol to the supernatant, collected by centrifugation, washed with 70% ethanol, and dried under vacuum. The dried pellet was resuspended in 1×TE buffer (1 mM EDTA, 10 mM Tris-HCl( pH 7.5)) and re-precipitated by adding lithium chloride to a final concentration of 2M. The pellet was resuspended in 1×TE buffer, and the RNA reprecipitated by adding 0.2 volumes of sodium acetate (pH 5.0) and 2.5 volumes of ethanol.

The Loblolly pine vicilin gene when transcribed produces a transcript of about 1.6 kB and the Loblolly pine vicilin seed storage polypeptide consists of about 523 amino acids (SEQ ID NOS 16 and 17; see FIGS. 2 and 3). Sequence homology searches were done with *Picea glauca* mRNA for vicilin-like storage protein emb (X63191) PGVICSP, SEQ ID NO:7, (Braun et al., *Plant Molec. Bio.,* 31:35–44, 1996), and *Zamia furfuracea* mRNA for vicilin-like SSP emb (Z50791) ZFVICLN7S, SEQ ID NO:8, (Newton et al., *Plant Mol. Biol.,* 20:315–322, 1992.) Sequence homology was determined using the National Center for Biotechnology Information's BLAST utility program, using default parameters.

The vicilin-like SSP gene from Loblolly pine has high nucleic acid homology (87%) with *Picea glauca* vicilin-like SSP gene, and 60% homology to *Zamia furfuacea* vicilin-like SSP gene. Neighbor joining analysis of the amino acid sequences of vicilin-like SSPs of various species demonstrates significant homology between species, especially in the center portion of the protein sequence. The amino terminus of the vicilin-like SSP shows less homology between each of the types of vicilin-like SSPs compared than at the carboxy terminus.

Example 2

Embryo Collection and Preparation

Loblolly pine cones were collected weekly from Boise Cascade's breeding orchard near Lake Charles, Louisiana. The cones were shipped on ice and received within 24–48 hours of collection. Cones were opened and seeds collected for isolation of embryos. Seeds were cracked using a hemostat, pried open with a scalpel, and the integument and nucellus tissue removed from the ovule. The female gametophyte was slit, pried open, and the dominant embryo/embryos or mass was removed. Embryos were evaluated for stage using a dissecting microscope. Stage 9 embryos were further characterized by the week they were collected. For example stage 9.1 refers to stage 9 embryos, collected week 1. Staged embryos were placed in cryostorage vials which were partially immersed in liquid nitrogen. Twenty similar stage embryos were collected and stored per vial. Frozen embryos were stored at −70° C. until further analysis was desired.

Example 3

Somatic Embryo Development and Vicilin-Like Promoters

Cultures of somatic embryos from loblolly pine may be initiated as described by Becwar et al. (*Can. J For. Res.,* 1990, 20:810) or by other commonly known techniques. Somatic embryos were grown in cell suspension culture medium 16 and maturation medium 240. Resulting somatic embryos were stored at −70° C. until needed.

RNA was obtained from cell suspension culture and somatic and zygotic embryos as described above and then fractionated by electrophoresis on a 1.2% agarose gel in the presence of formaldehyde and 10 mM sodium phosphate (pH 7.4)(Ausubel et al., *Current Protocols in Molecular Biology,* 1989, 231–233, John Wiley & Sons, New York). RNA was transferred to a positively charged Qiabrane membrane (Qiagen Corp., Chatsworth, Calif.) and hybridized with a nick translated $^{32}$P probe having the sequence of SEQ ID NO:19, excised from pRP37 using EcoRI. Plasmid pRP37 was the product of cloning the Loblolly pine vicilin cDNA (SEQ ID NO:16) into pCR2.1 (Invitrogen, Carlsbad, Calif.). The blot was hybridized with the probe ($10^7$ cpm/mL hybridization buffer) for 16 hours at 65° C. in the presence of 1% BSA, 1 mM EDTA, 5% SDS, sonicated salmon sperm DNA, and 0.5 M sodium phosphate buffer (pH 7.2). The filters were washed twice (30 min. each) at 60° C. with wash buffer containing 0.5% BSA, 5% SDS, 1 mM EDTA, and 40 mM sodium phosphate (pH 7.2). Two final washes were performed in a buffer containing 1% SDS, 1 mM EDTA, and 0.1×SSC at room temperature. To assess transfer efficiency, the same filters were hybridized with a probe (18S ribosomal RNA) constitutively expressed in Loblolly pine. A 0.5 Kb probe was excised from plasmid pRP18 with EcoRI for this purpose. Plasmid pRP18 was the product of cloning the 18S ribosomal DNA into pCR2.1 (Invitrogen, Carlsbad, Calif.). After drying, the filters were exposed to X-ray film (Kodak X-OMAT, Kodak, Rochester, N.Y.).

CsCl purified Loblolly pine DNA and tomato DNA were subjected to Southern hybridization. Genomic DNA was digested overnight with EcoRI and BamHI, separated by electrophoresis. A 1 Kb ladder (Promega, Madison, Wis.) was used as a molecular size marker. The digested DNA was transferred to Qiabrane nylon membrane (Qiagen, Chatsworth, Calif.) according to Sambrook et al., (Molecular Cloning, A Laboratory Manual, Cold Spring Harbor Laboratory Press, NY, 1989). Blots were hybridized with a radiolabeled probe consisting of the 1.4 Kb vicilin gene fragment from plasmid pRP37 following the protocol of Church et al., (Proc. Nat'l. Acad. Sci. USA. 1984, 81: 1991–1995) in a buffer containing 0.5 M sodium phosphate, 5% SDS, 10 mM EDTA (pH 7.2). Blots were then washed in the same buffer diluted 1:10. Probes were prepared according to the directions for the random primer labeling kit (Pharmacia, Piscataway, N.J.).

Several PCR fragments containing the vicilin gene were isolated using degenerate primers specifically designed to amplify developmentally regulated genes. From these clones, the most distal fragment sequences were used to prepare forward and reverse primers in order to obtain a maximum length (about 111.5Kb) vicilin cDNA.

Forward primer:
5'-GAGACGAGAAGAAGAGCGAGAG-3'(SEQ ID NO: 9) (DGfor)

Reverse primer:
5'-TGAAGTAGCAAGAGAAGAGCCC-3'(SEQ ID NO: 10) (DGback)

A 400 bp vicilin gene fragment was isolated from stage 8 zygotic embryos using PCR primers SEQ ID NOS: 9 and 10, above. From this fragment, the full length vicilin gene and cis regulatory elements (promoters) were isolated. A cDNA library from zygotic embryos was prepared using a cap finder PCR cDNA library construction kit (Clontech, Palo Alto, Calif.). The cDNA library consisted of 2.5×10$^6$ independent clones in Lambda gt 11 vectors. Sixty thousand Lambda clones from the library were screened with the 400 bp Loblolly pine vicilin fragment. Missing 3' sequences were obtained using the 3'RACE system (Gibco-BRL, Cat. No. 18373-019, Rockville, Md.). The gene specific primer used in the 3' RACE reaction was as follows:

5'-ACATGGTTGGTCTAGTCCGC-3' (SEQ ID NO:11) 3' race (Genosys Biotechnologies, The Woodlands, Tex.)

The promoter library was constructed using the Universal Genome Walker kit (Clontech, Palo Alto, Calif.). High molecular weight Loblolly pine genomic DNA was isolated from a fresh cell suspension culture 3 days after subculturing to new media using cell line BC #260, following the directions of Ausubel et al. Except PvuII, other enzymes digested the genomic DNA well. Primers were designed using Primer, Version 0.5 (Whitehead Inst. Of Biomedical Studies at MIT, Boston, Mass.). The following primers were used as gene specific primers for promoter screening:

5'-CGTAGACCACTGTACGCAGGAGACTGGTAA TG-3'; (SEQ ID NO:12) (Gsppro1);
5'-CTCCTTCCTCCAACTTTCTTTTCACCAGTTC-3'; (SEQ ID NO:13) (Gsppro2)

Modifications were made to the manufacturers' instructions for use of the Universal Genome Walker kit. The first seven cycles of Touch Down PCR for primary and secondary PCR were performed at 75° C. The desired PCR products, putative promoter fragments, SEQ ID NOS: 1–5, were gel purified and cloned into TA cloning vector 2.1 (Invitrogen, Carlsbad, Calif.), according to the manufacturer's protocol. Putative promoters pRP 5.1, pRP 5.2, pRP 5.3, pRP 5.4 and pRP 5.5 were sequenced using M13 forward and reverse primers located in the TA cloning vector 2.1.

RNA extraction was performed as described above. An extra step of RNA purification was performed using a column from the Plant RNA easy kit (Qiagen, Chatsworth, Calif.). One microgram of total RNA from each embryo developmental stage was used to prepare cDNA for the subsequent RT-PCR. Oligo dT$_{18}$, dNTPs, and MLV Reverse transcriptase was obtained from Clontech, Palo Alto. The reverse transcription reaction was incubated at 42° C. for one hour. Ten microliters of cDNA product was used for the RT-PCR reaction. Using SEQ ID NO:14 and SEQ ID NO:15, a 1.4 Kb gene fragment was amplified from the RT-PCR template following the manufacturer's instructions.

Forward primer:
5'-GAGACGAGAAGAAGAGCGAGAG-3' (SEQ ID NO:14)

Reverse primer:
5'-TGAAGTAGCAAGAGAAAGAGCCC-3' (SEQ ID NO:15)

Forward and reverse primers from 18S ribosomal RNA were used to verify the presence and amount of template for each RT-PCR reaction. (Quantum RNA 18S PCR Primers, Ambion, Austin, Tex.).

Initial isolation of vicilin-like seed storage gene was from stage 8 Loblolly pine zygotic embryos. Several degenerate primers were prepared to isolate developmentally regulated genes including MAD box like genes from Loblolly pine. Because of the high abundance of SSP transcripts in embryos, the Vicilin-like seed storage gene was isolated. In order to isolate the Vicilin-like seed storage gene, cDNA libraries from stage 3, 4, 5, 6, 7, 8 and 9 of Loblolly pine zygotic embryos were prepared using cap finder PCR cDNA library construction kits (Clontech, Palo Alto, Calif.).

Example 5

Delivery of Constructs to Plants and Monitoring Embryo Development

A plant embryo is transformed with a construct of a vicilin-like promoter operably linked to the gene encoding green fluorescent protein (or other reporter genes) using techniques as described in Miki et al., "Procedures for Introducing Foreign DNA into Plants", in Methods in Plant Molecular Biology and Biotechnolgy, Eds. BR Glick, JE Thompson, CRC Press, Inc. 1993. Constructs can also be delivered to plant embryos, especially to Loblolly pine, using the techniques described in Wenck et al., Plant Molecular Biology 39 (3):407–416 (1999).

The development of the embryo is assessed by monitoring levels of green fluorescent protein (or other reporter gene products) using a microscope or other appropriate reporter gene product detection means.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the following claims.

SEQUENCE LISTING

<160> NUMBER OF SEQ ID NOS: 19

<210> SEQ ID NO 1
<211> LENGTH: 341
<212> TYPE: DNA
<213> ORGANISM: Pinus taeda

<400> SEQUENCE: 1

| | | | | | | |
|---|---|---|---|---|---|---|
| actatagggc | acgcgtggtc | gacggcccgg | gctggtaaaa | gtgtgtgttt | gcagggtgca | 60 |
| gataatggca | gcatgtatga | cattagacat | atggcattgg | caaatgctgt | cgattttggc | 120 |
| actcatcact | gtaattgttg | caacatgtca | atcgtctgca | acatgccctg | gtgatcatag | 180 |
| gttatgcaag | aactcagacg | tgttcaccat | tcttcaatac | catatgcctc | ttctgtctgg | 240 |
| ttgcttccac | cacgcgtcca | tgcatgtgca | tgattctctt | gtatataaaa | gtcccccttg | 300 |
| cccattctgt | ctagtaccgg | acttcaccaa | agcaccatca | g | | 341 |

<210> SEQ ID NO 2
<211> LENGTH: 341
<212> TYPE: DNA
<213> ORGANISM: Pinus taeda

<400> SEQUENCE: 2

| | | | | | | |
|---|---|---|---|---|---|---|
| actatagggc | acgcgtggtc | gaggcccggg | ctggtaaaag | tgtgtgtttg | cagggtgcag | 60 |
| ataatggcag | catgtatgac | attagacata | tggcattggc | aaatgctgtc | gattttggca | 120 |
| ctcatcactg | taattgttgc | aacatgtcaa | tcgtccgcaa | catgccctgg | tgatcatagg | 180 |
| ttatgcaaga | actcagacgt | gttcaccgtt | cttcaatacc | aaatgcctct | tctgtctggt | 240 |
| tgcttccacc | acgcgtccat | gcatgtgcat | gattctcttg | tatataaaag | tcccccttgc | 300 |
| ccattctgtc | tagtaccgga | cttcaccaaa | gcaccatcat | g | | 341 |

<210> SEQ ID NO 3
<211> LENGTH: 340
<212> TYPE: DNA
<213> ORGANISM: Pinus taeda

<400> SEQUENCE: 3

| | | | | | | |
|---|---|---|---|---|---|---|
| actatagggc | acgcgtggtc | gacggcccgg | gctggtaaag | tgtgtgtttg | cagggtgcag | 60 |
| ataatggcag | catgtatgac | attagacata | tggcattggc | aaatgctatc | gattttggca | 120 |
| ctcatcactg | taattgttgc | aacatgtcaa | tcgtctgcag | catgccctgg | cgatcatagg | 180 |
| ttatgcaaga | actcagatgt | gttcaccatt | cttcaatacc | aaatgcctct | tctgtctggt | 240 |
| tgcttccacc | acgcgtccat | gcatgcacat | gattctcttg | tatataaaag | tcccccttgc | 300 |
| ccattctgtc | tagtaccgac | ttcaccaaag | caccatcatg | | | 340 |

<210> SEQ ID NO 4
<211> LENGTH: 340
<212> TYPE: DNA
<213> ORGANISM: Pinus taeda

<400> SEQUENCE: 4

| | | | | | | |
|---|---|---|---|---|---|---|
| actatagggc | acgcgtggtc | gacggcccgg | gtggtaaagt | gtgtgtttgc | agggtgcaga | 60 |
| taatggcagc | atgtatgaca | ttagacatat | ggcattggca | aatgctatcg | attttggcac | 120 |
| tcatcactgt | aattgttgca | acatgtcaat | cgtctgcaac | atgccctggc | gatcataggt | 180 |
| tatgcaagaa | ctcagatgag | ttcaccattc | ttcaatacca | aatgcctctt | ctgtctggtt | 240 |

```
gcttccacca cgcgtccatg catgcacatg attctcttgt atataaaagt cccccttgcc    300
cattctgtct agtaccagac ttcaccaaag caccatcatg                          340
```

<210> SEQ ID NO 5
<211> LENGTH: 565
<212> TYPE: DNA
<213> ORGANISM: Pinus taeda
<220> FEATURE:
<223> OTHER INFORMATION: n at 489 is a, c, g, or t
<223> OTHER INFORMATION: n at 503 is a, c, g, or t
<223> OTHER INFORMATION: n at 504 is a, c, g, or t
<223> OTHER INFORMATION: n at 522 is a, c, g, or t
<223> OTHER INFORMATION: n at 533 is a, c, g, or t
<223> OTHER INFORMATION: n at 543 is a, c, g, or t
<223> OTHER INFORMATION: n at 549 is a, c, g, or t
<223> OTHER INFORMATION: n at 564 is a, c, g, or t

<400> SEQUENCE: 5

```
actatagggc acgcgtggtc gacggcccgg gctggtaaaa attcatttac taatcaaaac     60
atgatgagat tcataaccaa agtctgttat aaaccatgat tataaccaac agattaacaa    120
tgatagaaca accattaaaa ccacataata acaagtacat ttacacatgg aacacaagag    180
gaaaatagct cttattaaca tatgaaaaat gtaactaggt caaggacttc cacgcaccaa    240
ccaaccatag attgggctga accaaatctt tctttcaact aatcacccct aagccatatt    300
cccagcatga atgtgggact acaaaaaaa caaacaagga ttccttagga tttaccataa    360
tccaccaagg gattcctagg cccaagccct catctataca actaggattt actgcaatcc    420
caccaaggga ttcctaagcc caaacaagaa acacacacta ccaggattta gataaacccc    480 ctttgtgggng ctgctatcag ctnngtttct tttaccttct gnatatcttc tgnggacacc    540
tgnctttana agccgattcc accnt                                          565
```

<210> SEQ ID NO 6
<211> LENGTH: 342
<212> TYPE: DNA
<213> ORGANISM: Artificial Sequence
<220> FEATURE:
<223> OTHER INFORMATION: Description of Artificial Sequence:consensus of
      sequences 1-4
<223> OTHER INFORMATION: n at 23 is c or no base
<223> OTHER INFORMATION: n at 32 is c or no base
<223> OTHER INFORMATION: n at 40 is a or no base
<223> OTHER INFORMATION: n at 157 is t or c
<223> OTHER INFORMATION: n at 161 is g or a
<223> OTHER INFORMATION: n at 172 is c or t
<223> OTHER INFORMATION: n at 199 is t or c
<223> OTHER INFORMATION: n at 223 is a or t
<223> OTHER INFORMATION: n at 267 is c or t
<223> OTHER INFORMATION: n at 268 is a or g
<223> OTHER INFORMATION: n at 319 is g, a, or no base.

<400> SEQUENCE: 6

```
actatagggc acgcgtggtc ganggcccgg gntggtaaan gtgtgtgttt gcagggtgca     60
gataatggca gcatgtatga cattagacat atggcattgg caaatgctgt cgattttggc    120
actcatcact gtaattgttg caacatgtca atcgtcngca ncatgccctg gngatcatag    180
gttatgcaag aactcagang tgttcaccat tcttcaatac canatgcctc ttctgtctgg    240
ttgcttccac cacgcgtcca tgcatgnnca tgattctctt gtatataaaa gtcccccttg    300
cccattctgt ctagtaccng acttcaccaa agcaccatca tg                       342
```

<210> SEQ ID NO 7
<211> LENGTH: 1590

<212> TYPE: DNA
<213> ORGANISM: Picea glauca

<400> SEQUENCE: 7

| | | | | | |
|---|---|---|---|---|---|
| caagcatcat | catggcttta | gcttctttac | ttatcattct | tcttgcaatc | tcctcctcct | 60 |
| cggctgccct | cactgagcca | ctagccagca | cggccaatcc | agaagttttt | cctgaatatc | 120 |
| tcggccgagg | ccgagggaga | cgagaagaag | agcgagagga | gaatccatat | gtattccaca | 180 |
| gtgacagctt | ccggaccaga | gcatcatctg | aagctggtga | aatcagagct | ctgccgaact | 240 |
| ttggggaggt | ctctgaactt | cttgaaggga | ttagaaaatt | cagagttacc | tgcattgaaa | 300 |
| tgaaacccaa | tacggtgatg | ctccctcact | atattgatgc | gacatggatc | ttatatgtta | 360 |
| ctagaggaag | aggttacata | gcctatgtgc | accagaatga | gctggttaaa | agaaagttgg | 420 |
| aggaaggaga | tgtattcggt | gttccaagtg | gtcatacatt | ttatctcgtt | aacaacgatg | 480 |
| accataacac | ccttcgcatt | gctagtctcg | tgcgtcccgt | gtctacggtc | cgaggagaat | 540 |
| atcagccctt | ctacgttgcg | ggaggtcgga | atcctcagac | tgtttactct | gcctttagcg | 600 |
| atgatgttct | cgaggctgca | ttcaatacga | acgtacagca | gcttgaacgt | attttcggtg | 660 |
| gacacaaaag | tggagtcata | atccacgcaa | atgaagaaca | gattagagaa | atgatgagga | 720 |
| aacgggatt | tcagcagga | tctatgtctg | cacctgagcc | ccccaagcct | ttcaaccttc | 780 |
| ggaaccagaa | gccagatttc | gagaacgaaa | atggcaggtt | tactattgct | ggtcccaaaa | 840 |
| attatccttt | tctagacgcg | ctcgacgttt | ctgttgggct | tgccgatttg | aatcctggat | 900 |
| ccatgacagc | cccatctctc | aactcgaaat | caacgtcaat | cggcattgtt | acgaatgggg | 960 |
| aaggaaggat | tgagatggcg | tgcccgcacc | ttggtcaaca | tggttggtct | agtccgcgcg | 1020 |
| agagaggcga | ccaagatatt | acctaccaga | gagtctgggc | aaagctgagg | accggcagcg | 1080 |
| tttatattgt | tcctgctggt | catccaatca | ccgagatagc | ttcaacaaac | agccgcctgc | 1140 |
| aaatcttgtg | gtttgatctt | aatacccgcg | gcaacgagag | acaattcctg | gcaggaaaga | 1200 |
| acaatgtgct | taacacgttg | gagagggaga | tcaggcagct | atccttcaac | gtaccacgtg | 1260 |
| gggaagagat | tgaagaagtg | ttgcaggcgc | aaaaggatca | agtcatcctg | agaggccccc | 1320 |
| aacgacgaag | ccgggacgag | gcgaggagct | cttcttagat | ccatgtcatc | atcgcagatc | 1380 |
| gcattatgga | cgacatgaca | agagtttctc | gacgttcact | cttaatatct | acttaaaaat | 1440 |
| aagctatcca | tatatgaagc | ccaataaatg | tgttcgaaga | tgaactcttt | ctgtctaaat | 1500 |
| gaatgtatgt | atgagtctaa | caaagctatc | gttgggctct | tctcttgcta | cttcaatgaa | 1560 |
| atggaatgca | gatcttctct | taaaaaaaaa | | | | 1590 |

<210> SEQ ID NO 8
<211> LENGTH: 1413
<212> TYPE: DNA
<213> ORGANISM: Zamia furfuracea

<400> SEQUENCE: 8

| | | | | | |
|---|---|---|---|---|---|
| tggtgggagg | ccgcaatcca | agggaccatg | gcccatctgt | gctctctacc | gctaatggca | 60 |
| gtgctaatgt | tgctgcttgc | atccgcttgc | ttttcggaat | tggaaataga | agatccctat | 120 |
| gtattcgacc | aacgcagctt | tgtgaccacg | gtacagtgta | aagccggtca | gatcagagct | 180 |
| ctacccaact | ttagcgccgg | cggcagatgt | gaattgccac | gagggcttgg | ggattatagc | 240 |
| gttgctcaga | taagcttgga | accgagatct | gtgctgcttc | ctcattatat | tgaggcagat | 300 |
| ttggctttat | acgtcacagg | aggaagagga | agggttgcgt | ttgttcatga | agagagactg | 360 |

```
gtagaaaggc agctgcggga cggagatgtg tacgcaattg ctgcaggtat accgttttat      420
attctcaaca cggatgacag tcggcgcctt ttcattcact gtctcctgcg cacgcagtgc      480
tctactaccg gactctatga gtcgttttac gtggtgggag gccgcaatcc gcagaatgtt      540
ttgtcccaat tcagcgagga cgttctgcaa gctgcattca acagttcgaa ggcggtcctg      600
gatcctatgc tggtaagtgg gtttaacaga ggggccataa ttagagtgtc cagagaacaa      660
atggaaaggc tgagcagggg tagaattaag ggattcggag ggtctgagga gccacagccc      720
ttcaacctgc tctacaggaa ccccgacttt ccaacaaca acggtgaaat tttcacagca       780
gacgccgcag atcatcgcgt tttacgccgg ctgaatgttg gagtgcagct tctcaactta      840
aagccgcgct caatgacggc accgcattac gatacaaggt cgaccagaat tggcatcgtt      900
aggaacggga ggggaatcct cgaattagtg cgcccgcaag aacaagaaca acaacaacaa      960
caacaacaag gtcccacata ccagaaacta cgggccaacc ttaaccccgg cactgttttc      1020
ctaacccgcc ccggctaccc ttccactgta attgcctctg gcaatgaggc attgcagata     1080
ttgtacctcg acaattattc ccaaggcagt cgcaggcaat tcctcgcagg aaggagcaat     1140
gtgttgagat atctgcctag ggaaattaag cgattggttt tcccatcttc cgctgaggag     1200
atagaggcaa ccttggaagc gcaggaagat gaggttctcc tcaacgcgca acaagggcgg     1260
gccgaccagt agtagagaaa ccgtggactc cacttggtgc ggctcagtat aaacatatgg     1320
acttctccct agtaccttgc cctgtacagc tcgtcgttct ccatacccac ggaaataaat     1380
aaatgggatc ttgcctcgca tccgcacccc ttt                                  1413

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 9
gagacgagaa gaagagcgag ag                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 10
tgaagtagca agagaagagc cc                                              22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:3' RACE
      primer

<400> SEQUENCE: 11
acatggttgg tctagtccgc                                                 20

<210> SEQ ID NO 12
<211> LENGTH: 32
<212> TYPE: DNA
<213> ORGANISM: Artificial Sequence
<220> FEATURE:
```

<223> OTHER INFORMATION: Description of Artificial Sequence:Gene
      Specific Primer

<400> SEQUENCE: 12
cgtagaccac tgtacgcagg agactggtaa tg                                     32

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:Gene
      Specific Primer

<400> SEQUENCE: 13
ctccttcctc caactttctt ttcaccagtt c                                      31

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 14
gagacgagaa gaagagcgag ag                                                22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 15
tgaagtagca agagaaagag ccc                                               23

<210> SEQ ID NO 16
<211> LENGTH: 1581
<212> TYPE: DNA
<213> ORGANISM: Pinus taeda

<400> SEQUENCE: 16
aaagcaccat catggctttt gtttctttac ttaccattct tcaagcaatc tcctcctgct        60
ccgttgctct cactgagcca ctagccactg tggccaatca aggagttttt cctgaagatc       120
atgggcgagg gcaccagaga cgagaagaag aacgagagga gaatccgtac gtattccaca       180
gtgacagatt caggatgaga gcgtcatctg acgctggtga aatcagagct ctccccaact       240
ttggtgaggc ctctgaactt cttgaaggga ttagtaaata cagagttacc tgcattgaaa       300
tgagacccaa cacggtcatg ctccctcact atcttgacgc gacatggatt ttatatgtta       360
ctggaggaag aggttacata gcttacgtgc accagaatga actggtgaaa agaaagttgg       420
aggaaggaga tgtatttggt gttccaagtg gtcatacatt ttatctcgtt aacaacgatg       480
accacaacag ccttcgcatt accagtctcc tgcgtacagt gtctacgatg cgaggagaat       540
atgagcccta ctacgttgct ggaggtcgga atcctgagac tgtttactct gcctttagcg       600
atgatgttct cgaagctgca ttcaatacga acgttataga agctagaaca catttttccgg     660 tgcacataga acgggagtca tattccatgg caaatgaaga acagattaga gaatgttga       720 ggaaacgggg attttcagca gaatccatgt ctgcatctga gcacccaaag ccttttaacc       780
ttcggaacca gaagccagat ttcgagaacg acaatggcag gtttactaga gctggtccca       840

```
atgaaaatcc tcttcttgac gcggtcgatg ttactgctgg gtttggcgtt ttgaatcctg    900
gaaccatgac agccccatct cacaacacga aagcaacctc aatcgccatt gtcacacagg    960
gggagggaag gattgagatg gcgtgcccgc accttggtca acatggctgg tctagtcggc   1020
gcgagaaagg cgatcaggaa attaattacc agagggtacg ggcaaggctg agaaccggca   1080
ccgtttacgt tgttcctgca ggtcatccaa tcaccgagat agcttgcaca gagggccacc   1140
ttgaaatctt gtggtttgat attaatacga gcggcaacga gagacaattc ctggcaggaa   1200
agtacaatgt gcttcaaacg ctggagaagg aggtcaggca gatatccttc aacataccac   1260
gtggggaaga gctggatgaa gttttacggc ggcaaaagga tcaagtcatc ctcagagggc   1320
cccaaatgca aaggcgagac gagccaagga gctcttctta gatccatgcc atcatcgcag   1380
ctcgcatcat ggacgacaag actagagttt ctccacgttc actctttagt atctacttaa   1440
gaataagtta tgcatatatg aagcccaaaa aatgtgttcg aagatgagct ccttttatct   1500
taatgaatgt atatatgagt ttcaacaaac ctatcgttgg gctcttctct tgctacttca   1560
atgacatgga atgctgatct t                                             1581
```

<210> SEQ ID NO 17
<211> LENGTH: 523
<212> TYPE: PRT
<213> ORGANISM: Pinus taeda

<400> SEQUENCE: 17

```
Ser Thr Ile Met Ala Phe Val Ser Leu Leu Thr Ile Leu Gln Ala Ile
  1               5                  10                  15

Ser Ser Cys Ser Val Ala Leu Thr Glu Pro Leu Ala Thr Val Ala Asn
             20                  25                  30

Gln Gly Val Phe Pro Glu Asp His Gly Arg Gly His Gln Arg Arg Glu
         35                  40                  45

Glu Glu Arg Glu Glu Asn Pro Tyr Val Phe His Ser Asp Arg Phe Arg
     50                  55                  60

Met Arg Ala Ser Ser Asp Ala Gly Glu Ile Arg Ala Leu Pro Asn Phe
 65                  70                  75                  80

Gly Glu Ala Ser Glu Leu Leu Glu Gly Ile Ser Lys Tyr Arg Val Thr
                 85                  90                  95

Cys Ile Glu Met Arg Pro Asn Thr Val Met Leu Pro His Tyr Leu Asp
            100                 105                 110

Ala Thr Trp Ile Leu Tyr Val Thr Gly Gly Arg Gly Tyr Ile Ala Tyr
        115                 120                 125

Val His Gln Asn Glu Leu Val Lys Arg Lys Leu Glu Glu Gly Asp Val
    130                 135                 140

Phe Gly Val Pro Ser Gly His Thr Phe Tyr Leu Val Asn Asn Asp Asp
145                 150                 155                 160

His Asn Ser Leu Arg Ile Thr Ser Leu Leu Arg Thr Val Ser Thr Met
                165                 170                 175

Arg Gly Glu Tyr Glu Pro Tyr Tyr Val Ala Gly Gly Arg Asn Pro Glu
            180                 185                 190

Thr Val Tyr Ser Ala Phe Ser Asp Asp Val Leu Glu Ala Ala Phe Asn
        195                 200                 205

Thr Asn Val Ile Glu Ala Arg Thr His Phe Pro Val His Ile Glu Arg
    210                 215                 220

Glu Ser Tyr Ser Met Ala Asn Glu Glu Gln Ile Arg Glu Met Leu Arg
225                 230                 235                 240
```

-continued

```
Lys Arg Gly Phe Ser Ala Glu Ser Met Ser Ala Ser Glu His Pro Lys
                245                 250                 255

Pro Phe Asn Leu Arg Asn Gln Lys Pro Asp Phe Glu Asn Asp Asn Gly
            260                 265                 270

Arg Phe Thr Arg Ala Gly Pro Asn Glu Asn Pro Leu Leu Asp Ala Val
            275                 280                 285

Asp Val Thr Ala Gly Phe Gly Val Leu Asn Pro Gly Thr Met Thr Ala
        290                 295                 300

Pro Ser His Asn Thr Lys Ala Thr Ser Ile Ala Ile Val Thr Gln Gly
305                 310                 315                 320

Glu Gly Arg Ile Glu Met Ala Cys Pro His Leu Gly Gln His Gly Trp
                325                 330                 335

Ser Ser Arg Arg Glu Lys Gly Asp Gln Glu Ile Asn Tyr Gln Arg Val
            340                 345                 350

Arg Ala Arg Leu Arg Thr Gly Thr Val Tyr Val Val Pro Ala Gly His
            355                 360                 365

Pro Ile Thr Glu Ile Ala Cys Thr Glu Gly His Leu Glu Ile Leu Trp
        370                 375                 380

Phe Asp Ile Asn Thr Ser Gly Asn Glu Arg Gln Phe Leu Ala Gly Lys
385                 390                 395                 400

Tyr Asn Val Leu Gln Thr Leu Glu Lys Glu Val Arg Gln Ile Ser Phe
                405                 410                 415

Asn Ile Pro Arg Gly Glu Glu Leu Asp Glu Val Leu Arg Arg Gln Lys
            420                 425                 430

Asp Gln Val Ile Leu Arg Gly Pro Gln Met Gln Arg Arg Asp Glu Pro
        435                 440                 445

Arg Ser Ser Ile His Ala Ile Ala Ala Arg Ile Met Asp Asp
450                 455                 460

Lys Thr Arg Val Ser Pro Arg Ser Leu Phe Ser Ile Tyr Leu Arg Ile
465                 470                 475                 480

Ser Tyr Ala Tyr Met Lys Pro Lys Lys Cys Val Arg Arg Ala Pro Phe
                485                 490                 495

Ile Leu Met Asn Val Tyr Met Ser Phe Asn Lys Pro Ile Val Gly Leu
            500                 505                 510

Phe Ser Cys Tyr Phe Asn Asp Met Glu Cys Ser
            515                 520

<210> SEQ ID NO 18
<211> LENGTH: 448
<212> TYPE: PRT
<213> ORGANISM: Picea glauca

<400> SEQUENCE: 18

Met Ala Leu Ala Ser Leu Leu Ile Ile Leu Leu Ala Ile Ser Ser Ser
  1               5                  10                  15

Ser Ala Ala Leu Thr Glu Pro Leu Ala Ser Thr Ala Asn Pro Glu Val
             20                  25                  30

Phe Pro Glu Tyr Leu Gly Arg Gly Arg Gly Arg Arg Glu Glu Glu Arg
         35                  40                  45

Glu Glu Asn Pro Tyr Val Phe His Ser Asp Ser Phe Arg Thr Arg Ala
     50                  55                  60

Ser Ser Glu Ala Gly Glu Ile Arg Ala Leu Pro Asn Phe Gly Glu Val
 65                 70                  75                  80

Ser Glu Leu Leu Glu Gly Ile Arg Lys Phe Arg Val Thr Cys Ile Glu
```

|     |     |     | 85  |     |     |     | 90  |     |     |     | 95  |     |
| --- | --- | --- | --- | --- | --- | --- | --- | --- | --- | --- | --- | --- |
| Met | Lys | Pro | Asn | Thr | Val | Met | Leu | Pro | His | Tyr | Ile | Asp | Ala | Thr | Trp |
|     |     |     |     | 100 |     |     |     | 105 |     |     |     | 110 |

Met Lys Pro Asn Thr Val Met Leu Pro His Tyr Ile Asp Ala Thr Trp
                100                 105                 110

Ile Leu Tyr Val Thr Arg Gly Arg Gly Tyr Ile Ala Tyr Val His Gln
            115                 120                 125

Asn Glu Leu Val Lys Arg Lys Leu Glu Glu Gly Asp Val Phe Gly Val
130                 135                 140

Pro Ser Gly His Thr Phe Tyr Leu Val Asn Asn Asp His Asn Thr
145                 150                 155                 160

Leu Arg Ile Ala Ser Leu Val Arg Pro Val Ser Thr Val Arg Gly Glu
                165                 170                 175

Tyr Gln Pro Phe Tyr Val Ala Gly Gly Arg Asn Pro Gln Thr Val Tyr
            180                 185                 190

Ser Ala Phe Ser Asp Asp Val Leu Glu Ala Ala Phe Asn Thr Asn Val
                195                 200                 205

Gln Gln Leu Glu Arg Ile Phe Gly Gly His Lys Ser Gly Val Ile Ile
210                 215                 220

His Ala Asn Glu Glu Gln Ile Arg Glu Met Met Arg Lys Arg Gly Phe
225                 230                 235                 240

Ser Ala Gly Ser Met Ser Ala Pro Glu His Pro Lys Pro Phe Asn Leu
                245                 250                 255

Arg Asn Gln Lys Pro Asp Phe Glu Asn Glu Asn Gly Arg Phe Thr Ile
                260                 265                 270

Ala Gly Pro Lys Asn Tyr Pro Phe Leu Asp Ala Leu Asp Val Ser Val
                275                 280                 285

Gly Leu Ala Asp Leu Asn Pro Gly Ser Met Thr Ala Pro Ser Leu Asn
290                 295                 300

Ser Lys Ser Thr Ser Ile Gly Ile Val Thr Asn Gly Glu Gly Arg Ile
305                 310                 315                 320

Glu Met Ala Cys Pro His Leu Gly Gln His Gly Trp Ser Ser Pro Arg
                325                 330                 335

Glu Arg Gly Asp Gln Asp Ile Thr Tyr Gln Arg Val Trp Ala Lys Leu
                340                 345                 350

Arg Thr Gly Ser Val Tyr Ile Val Pro Ala Gly His Pro Ile Thr Glu
                355                 360                 365

Ile Ala Ser Thr Asn Ser Arg Leu Gln Ile Leu Trp Phe Asp Leu Asn
370                 375                 380

Thr Arg Gly Asn Glu Arg Gln Phe Leu Ala Gly Lys Asn Asn Val Leu
385                 390                 395                 400

Asn Thr Leu Glu Arg Glu Ile Arg Gln Leu Ser Phe Asn Val Pro Arg
                405                 410                 415

Gly Glu Glu Ile Glu Glu Val Leu Gln Ala Gln Lys Asp Gln Val Ile
                420                 425                 430

Leu Arg Gly Pro Gln Arg Arg Ser Arg Asp Glu Ala Arg Ser Ser Ser
                435                 440                 445

```
<210> SEQ ID NO 19
<211> LENGTH: 1596
<212> TYPE: DNA
<213> ORGANISM: Artificial Sequence
<220> FEATURE:
<223> OTHER INFORMATION: Description of Artificial Sequence:Vicilin-like
      gene with TA linkers

<400> SEQUENCE: 19
```

-continued

```
aattcggctt aaagcaccat catggctttt gtttctttac ttaccattct tcaagcaatc      60
tcctcctgct ccgttgctct cactgagcca ctagccactg tggccaatca aggagttttt     120
cctgaagatc atgggcgagg gcaccagaga cgagaagaag aacgagagga gaatccgtac     180
gtattccaca gtgacagatt caggatgaga gcgtcatctg acgctggtga aatcagagct     240
ctccccaact ttggtgaggc ctctgaactt cttgaaggga ttagtaaata cagagttacc     300
tgcattgaaa tgagacccaa cacggtcatg ctccctcact atcttgacgc gacatggatt     360
ttatatgtta ctggaggaag aggttacata gcttacgtgc accagaatga actggtgaaa     420
agaaagttgg aggaaggaga tgtatttggt gttccaagtg gtcatacatt ttatctcgtt     480
aacaacgatg accacaacag ccttcgcatt accagtctcc tgcgtacagt gtctacgatg     540
cgaggagaat atgagcccta ctacgttgct ggaggtcgga atcctgagac tgtttactct     600
gcctttagcg atgatgttct cgaagctgca ttcaatacga acgttataga agctagaaca     660
cattttccgg tgcacataga acgggagtca tattccatgg caaatgaaga acagattaga     720
gaaatgttga ggaaacgggg attttcagca gaatccatgt ctgcatctga gcacccaaag     780
ccttttaacc ttcggaacca gaagccagat ttcgagaacg acaatggcag gtttactaga     840
gctggtccca atgaaaatcc tcttcttgac gcggtcgatg ttactgctgg gtttggcgtt     900
ttgaatcctg gaaccatgac agccccatct cacaacacga aagcaacctc aatcgccatt     960
gtcacacagg gggagggaag gattgagatg gcgtgcccgc accttggtca acatggctgg    1020
tctagtcggc gcgagaaagg cgatcaggaa attaattacc agagggtacg ggcaaggctg    1080
agaaccggca ccgtttacgt tgttcctgca ggtcatccaa tcaccgagat agcttgcaca    1140
gagggccacc ttgaaatctt gtggtttgat attaatacga gcggcaacga gagacaattc    1200
ctggcaggaa agtacaatgt gcttcaaacg ctggagaagg aggtcaggca gatatccttc    1260
aacataccac gtggggaaga gctggatgaa gttttacggc ggcaaaagga tcaagtcatc    1320
ctcagagggc cccaaatgca aaggcgagac gagccaagga gctcttctta gatccatgcc    1380
atcatcgcag ctcgcatcat ggacgacaag actagagttt ctccacgttc actctttagt    1440
atctacttaa gaataagtta tgcatatatg aagcccaaaa aatgtgttcg aagatgagct    1500
ccttttatct taatgaatgt atatatgagt ttcaacaaac ctatcgttgg gctcttctct    1560
tgctacttca atgacatgga atgctgatct tagccg                              1596
```

What is claimed is:

1. An isolated promoter comprising a nucleic acid selected from the group consisting of
(a) a nucleic acid molecule having a nucleotide sequence selected from the group consisting of SEQ ID NOS:1–6; and
(b) a nucleic acid molecule of from 100 to 400 nucleotides, which is a fragment of (a), wherein the fragment retains promoter activity of (a).

2. The isolated promoter of claim 1 wherein the isolated promoter is operably linked to a DNA sequence encoding a desired polypeptide.

3. The isolated promoter of claim 1, wherein the nucleic acid molecule has the nucleotide sequence of SEQ ID NO:1.

4. A fragment of the isolated promoter of claim 1, wherein The fragment retains promoter activity, and wherein the fragment has a nucleotide sequence which is a portion of SEQ ID NO:1.

5. The isolated promoter of claim 2, wherein the isolated promoter is a vicilin promoter.

6. The isolated promoter of claim 5, wherein the isolated promoter has a nucleotide sequence selected from the group consisting of SEQ ID NOS:1–6.

7. The isolated promoter of claim 6, wherein the isolated promoter has the nucleotide sequence of SEQ ID NO:1.

8. A method of expressing a desired polypeptide in a plant, comprising the step of transforming said plant with a promoter-gene construct comprising a promoter selected from the group consisting of SEQ ID NOS:1–6 operably linked to a desired DNA sequence encoding the desired polypeptide, whereby the desired polypeptide is expressed in the plant.

9. The method of claim 8 wherein said polypeptide is a structural protein.

10. The method of claim 8 wherein said polypeptide is a seed storage protein (SSP).

11. The method of claim 8 wherein said DNA sequence is selected from the group consisting of a hererologous DNA sequence and a non-heterologous DNA sequence.

12. The method of claim 11 wherein said heterologous DNA sequence is a reporter DNA sequence encoding a protein selected from the group consisting of green fluorescent protein, alkaline phosphatase, chloramphenicol acetyltransferase, B-glucuronidase, firefly luciferase, bacterial luciferase and β-galactosidase.

13. The method of claim 8 wherein said promoter comprises a nucleic acid molecule having the sequence of SEQ ID NO:1.

14. The method of claim 8 wherein the promoter is inducible, and further comprising the step of inducing expression of said DNA sequence with an inducer.

15. The method of claim 14 wherein said inducer is selected from the group consisting of ABA, heat, and light.

16. A method expressing a desired polypeptide in plant, comprising the step of transforming said plant with a promoter-gene construct comprising a nucleic acid molecule fragment having a nucleotide sequence of from 100 to 400 nucleotides selected from the group consisting of SEQ ID NO:1–6 and operably linked to a DNA sequence encoding the desired polypeptide wherein said fragment retains promoter activity wherein the fragment retaims promoter activity nucleic acid molecule haxing a sequence selected from teh group consisting of SEQ ID NO:1–6.

17. A method of monitoring embryo development of a plant embryo comprising the step of transforming said embryo with a promoter-gene construct comprising a promoter selected from the group consisting of SEQ ID NOS: 1–6 operably linked to a reporter DNA sequence and monitoring the level of expression of said reporter DNA sequence, whereby expression of the reporter DNA sequence provides a quantitative marker for monitoring embryo development.

18. The method of claim 17 wherein said reporter DNA sequence encodes a protein selected from the group consisting of green fluorescent protein, alkaline phosphatase, chloramphenicol acetyltransferase, B-glucuronidase, firefly luciferase, bacterial luciferase, and β-galactosidase.

19. A transgenic plant comprising a promoter operably linked to a desired DNA sequence, wherein said promoter is selected from the group consisting of SEQ ID Nos: 1–6.

20. The plant of claim 15 wherein said plant is a gymnosperm.

21. The plant of claim 20 wherein said gymnosperm is a conifer.

22. A transgenic plant comprising the promoter of claim 1.

23. A transgenic plant comprising the promoter of claim 7.

* * * * *

UNITED STATES PATENT AND TRADEMARK OFFICE
CERTIFICATE OF CORRECTION

PATENT NO.    : 6,462,257 B1
DATED         : October 8, 2002
INVENTOR(S)   : Ranjan Perera, John Cairney and Gerald S. Pullman It is certified that error appears in the above-identified patent and that said Letters Patent is hereby corrected as shown below:

Title page, Item [54] and Column 1, line 1,
Title, please delete "VICILIN-LIKE" and insert -- VICILIN -- therefor.

Title page,
Item [56], References Cited, OTHER PUBLICATIONS, please insert
-- Reynolds, "Inducible control of Gene Expression: an Overview", *Inducible Gene Expression in Plants* 1999 1-9 --.

Column 1,
Line 46, please delete "Panget al." and insert -- Pang et al. -- therefor.

Column 3,
Line 32, please insert -- be -- after "may" and before "heterologous".

Column 11,
Line 20, please delete "(about 111.5Kb)" and insert -- (about 1.5 Kb) -- therefor.

Column 30,
Line 56, please insert -- and -- after "1-6" and before "operably".
Line 57, please delete "desired".
Line 11, please delete "hererologous" and insert -- heterologous -- therefor .

Column 31,
Line 13, please insert -- a -- after "in" and before "plant".
Line 19, please insert -- , -- after "polypeptide" and please delete "said" and insert -- the -- therefor.

UNITED STATES PATENT AND TRADEMARK OFFICE
CERTIFICATE OF CORRECTION

PATENT NO. : 6,462,257 B1
DATED : October 8, 2002
INVENTOR(S) : Ranjan Perera, John Cairney and Gerald S. Pullman It is certified that error appears in the above-identified patent and that said Letters Patent is hereby corrected as shown below:

Column 31 (cont'd),
Lines 20-22, please delete "wherein the fragment retaims promoter activity nucleic acid molecule haxing a sequence selected from teh group consisting of SEQ ID No:1-6." and insert -- and whereby the desired polypeptide is expressed in the plant. --

Signed and Sealed this

Ninth Day of August, 2005

JON W. DUDAS
*Director of the United States Patent and Trademark Office*